United States Patent
Valable et al.

(10) Patent No.: US 11,446,626 B2
(45) Date of Patent: Sep. 20, 2022

(54) PROCESS FOR THE PREPARATION OF A SUSPENSION OF NANOSIZED SYNTHETIC ZEOLITE MATERIALS, SUSPENSIONS OF NANOSIZED SYNTHETIC ZEOLITE MATERIALS OBTAINED BY SAID PROCESS AND THEIR USES IN THERAPY AND DIAGNOSIS

(71) Applicants: CENTRE NATIONAL DE LA RECHERCHE SCIENTIFIQUE, Paris (FR); UNIVERSITE DE CAEN NORMANDIE, Caen (FR)

(72) Inventors: Samuel Valable, Colomby-Anguerny (FR); Svetlana Mintova Lazarova, Basly (FR); Clément Anfray, Thaon (FR); Valentin Valtchev, Basly (FR); Omar Touzani, Villy-Bocage (FR); Myriam Bernaudin, Bernières-sur-Mer (FR)

(73) Assignees: CENTRE NATIONAL DE LA RECHERCHE SCIENTIFIQUE, Paris (FR); UNIVERSITE DE CAEN NORMANDIE, Caen (FR)

( * ) Notice: Subject to any disclaimer, the term of this patent is extended or adjusted under 35 U.S.C. 154(b) by 179 days.

(21) Appl. No.: 16/636,735

(22) PCT Filed: Aug. 7, 2018

(86) PCT No.: PCT/EP2018/071332
§ 371 (c)(1),
(2) Date: Jun. 22, 2020

(87) PCT Pub. No.: WO2019/030200
PCT Pub. Date: Feb. 14, 2019

(65) Prior Publication Data
US 2020/0238242 A1 Jul. 30, 2020

(30) Foreign Application Priority Data
Aug. 8, 2017 (EP) .................................... 17306054

(51) Int. Cl.
*B01J 13/00* (2006.01)
*A61K 49/18* (2006.01)
*C01B 39/46* (2006.01)
*A61K 9/00* (2006.01)
*B82Y 5/00* (2011.01)

(52) U.S. Cl.
CPC ....... *B01J 13/0039* (2013.01); *A61K 49/1806* (2013.01); *C01B 39/46* (2013.01); *A61K 9/0019* (2013.01); *B82Y 5/00* (2013.01)

(58) Field of Classification Search
None
See application file for complete search history.

(56) References Cited

FOREIGN PATENT DOCUMENTS

| FR | 2865663 A1 | 8/2005 |
|----|------------|--------|
| WO | 0240403 A1 | 5/2002 |
| WO | 2005123587 A2 | 12/2005 |
| WO | 2016166245 A1 | 10/2016 |
| WO | 2017068387 A1 | 4/2017 |

OTHER PUBLICATIONS

Clement Anfray, "Acute Toxicity of Silver Free and Encapsulated in Nanosized Xeolite for Eukaryotic Cells", Applied Viatrials & Interfaces, 2017 American Chemical Society, 13849-13854.
International Search Report for corresponding application PCT/EP2018071332 filed Aug. 7, 2018; dated Aug. 29, 2018.
L. Lakiss, "Copper-Containing Nanoporous Fils", Superlattices and Microstructures (2008) 617-625.
Svetlana Mintova, "Nanosized microporous crystals: emerging application", The Royal Society of Chemistry, 2015.
Written Opinion for corresponding application PCT/EP2018071332 filed Aug. 7, 2018; dated Aug. 29, 2018.

*Primary Examiner* — Robert S Cabral
(74) *Attorney, Agent, or Firm* — Cantor Colburn LLP

(57) ABSTRACT

The present invention relates to a method for the preparation of a colloidal aqueous suspension of stable zeolite nanocrystals having framework structures comprising at least one cation selected from Gd, Fe, Cu and Ce, said structures being loaded with a gas selected from $O_2$, $CO_2$ and mixtures thereof, to the colloidal aqueous suspension of zeolite nanocrystals obtained by such a process, and to the use of said suspension in therapy, more particularly in cancer therapy and hypoxia-related diseases and/or in diagnosis.

22 Claims, 11 Drawing Sheets

C

PROCESS FOR THE PREPARATION OF A SUSPENSION OF NANOSIZED SYNTHETIC ZEOLITE MATERIALS, SUSPENSIONS OF NANOSIZED SYNTHETIC ZEOLITE MATERIALS OBTAINED BY SAID PROCESS AND THEIR USES IN THERAPY AND DIAGNOSIS

The present invention relates to a method for the preparation of a colloidal aqueous suspension of stable zeolite nanocrystals having framework structures comprising at least one cation selected from Gd, Fe, Cu and Ce, said structures being loaded with a gas selected from $O_2$, $CO_2$ and mixtures thereof, to the colloidal aqueous suspension of zeolite nanocrystals obtained by such a process, and to the use of said suspension in therapy, more particularly in cancer therapy and hypoxia-related diseases and/or in diagnosis.

Oxygen is a vital element of the human being and cell function. Oxygen is delivered to the organs through the blood and a continuous blood supply is mandatory for cell survival. Although the brain represents only 2% of the body weight, it receives 15% of the cardiac output, and 20% of the total body oxygen consumption. With a global blood flow of 57 ml/100 g/min, the brain extracts approximately 40% of oxygen from the arterial blood. The brain is completely dependent upon this continuous supply of oxygen via the regulation of the cerebral blood flow. As a consequence, a discontinuation in the blood flow or a dysregulation between oxygen consumption and availability (as it is occurring for example in stroke and heart attack), well known as hypoxia, leads to brain dysfunction and death.

Hypoxia is also a feature of aggressive solid tumors and it has been long appreciated that tumor sensitivity to radiotherapy is oxygen-dependent. In particular, hypoxia is one of the main cause of resistance to treatments in glioblastoma (GB), the worst primary brain tumor in term of survival [Louis, D. N. et al., The 2016 World Health Organization Classification of Tumors of the Central Nervous System: a summary. *Acta Neuropathol.* (*Berl.*)131, 803-820 (2016)]. It is also known that hypoxia is a major factor for tumoral angiogenesis, tumor aggressiveness, patient survival and local recurrence and metastasis.

Organ transplantation is also a field where oxygen deficiency is responsible for organ irreversible damage and new technologies that could help to decrease the deterioration of graft could substantially increase the availability of grafts.

Several approaches have already been used to improve oxygen concentration so as, for instance, to resensitize hypoxic tumors such as red blood cell transplantation, breathing of hyperbaric oxygen or breathing of a mixture composed of 5% $CO_2$ balanced in 95% oxygen (called "carbogen") treatment that were thought to alleviate tumor hypoxia. However, these approaches have been largely unsuccessful or even counter-effective. In particular, regarding the use of carbogen, the overall results were unsatisfactory in terms of sensitization to radiotherapy in brain tumors [van der Maazen, R. W. M. et al. Conventional radiotherapy combined with carbogen breathing and nicotinamide for malignant gliomas. *Radiother. Oncol.* 35, 118-122 (1995)].

In a recent study using multiparametric magnetic resonance imaging (MRI) to simultaneously assess the cerebral blood volume (CBV) and brain oxygenation, it has been demonstrated that administration of carbogen was very effective to increase the CBV and the oxygenation in the healthy tissue, but that this increase was much more moderate in the tumor due to compensatory mechanisms between the normal and the tumoral tissues where it is greatly dependent on the vasodilatory capacity [Chakhoyan, A. et al. Carbogen-induced increases in tumor oxygenation depend on the vascular status of the tumor: A multiparametric MRI study in two rat glioblastoma models. *J. Cereb. Blood Flow Metab. Off. J. Int. Soc. Cereb. Blood Flow Metab.* (2016). doi:10.1177/0271678X16663947].

It has also been proposed, in particular by R. P. Seekell et al., (PNAS, Oxygen delivery using engineered microparticles, Nov. 1, 2016, vol. 113, n°44, 12380-12385) to use thin-walled polymer hollow microcapsules with nanoporous shell to charge oxygen gas and release it when exposed to desaturated blood. Even if these polymer microcapsules are able to deliver approximately five times more oxygen that human red blood cells (per gram), their use to reduce hypoxia in brain tumors is also not satisfactory because they have too high diameter (mean diameter of about 8-10 µm) to reach brain tumors, since they are too big to pass through the walls of blood vessels irrigating the tumors following intravenous injection. Their size also disables any intravenous injection since it may cause vascular obstruction. In addition, according to the preparation process used, it is not possible to access to microcapsules having nanometer dimensions that would allow them to pass through the walls of blood vessels irrigating the tumors.

Parallelly, in recent years, a growing interest has focused on the use of nanoparticles (NP) as vectors of contrast agents and therapies, especially in the context of diagnosis and treatments of cancer[6] and particularly in GB[7]. One of the reason of this interest for NP is their ability to accumulate preferentially in tumor tissue through the EPR (Enhanced Permeability and Retention) effect[8].

Among NP, studies for biomedical applications have focused on a class of materials called zeolites crystals. Zeolites and zeolite-like materials comprise a broad range of porous crystalline solids. The structures of zeolite-type materials are essentially based on tetrahedral networks which encompass channels and cavities. According to ©2001 IUPAC [*Pure Appl. Chem.*, 2001, 73, 2, 381-394], microporous crystalline materials with an inorganic, three-dimensional host structure composed of fully linked, corner-sharing tetrahedra and the same host topology constitute a zeolite framework type. The number of established framework or structure types has increased progressively in the last 4 to 5 decades of highly active research in the field of zeolites. Currently, the number of established structure types is clearly in excess of 233. All zeolite structure types are referenced with three capital letter codes. They have different framework densities, chemical compositions, dimensional channel systems and thus, different properties.

Zeolites are generally characterized by their high specific surface areas, high micropore volume, and capacity to undergo cation exchange. Therefore, they can be used in various applications, for example as catalysts (heterogeneous catalysis), absorbents, ion-exchangers, and membranes, in many chemical and petrochemical processes (e.g. in oil refining, fine- and petro-chemistry).

Most of the described zeolites are aluminosilicate zeolites and basically comprise a three-dimensional framework of $SiO_4$ and $AlO_4$ tetrahedra. The electroneutrality of each tetrahedra containing aluminum is balanced by the inclusion in the crystal of a metallic cation, for example a sodium cation. The micropore spaces (channels and cavities) are occupied by water molecules prior to dehydration.

Over the past decade, renewed efforts were devoted to prepare zeolites with enhanced accessibility to their micropores, including post-synthesis modification, one-step hydrothermal crystallization in the presence of mesopore modifiers and synthesis of nanosized zeolite crystals with or without organic templates. The interest in the preparation of nanosized zeolites has gradually increased, but only 24 from the 233 structures known to date have so far been synthesized with nanosized dimensions and stabilized in colloidal suspensions. Indeed, the particle size reduction of zeolites to the nanometer scale leads to substantial changes in their properties such as increased external surface area and decreased diffusion path lengths (which can lead to pore blocking by coke formation). More particularly, the specific conditions employed to lead to nanosized zeolites change their intrinsic characteristics, impeding the full use of their potential, in particular their sorption properties and thus their ability to encapsulate gases such as NO, $CO_2$, and $O_2$.

Up to now, no zeolite material has been particularly designed to be used in biological applications, in particular to target tissues in need of reoxygenation.

Consequently, there is still a need for high quality nanosized, biocompatible zeolite materials particularly suited for gas adsorption/desorption.

More particularly, the aim of the present invention is to provide an efficient and simple preparation method which leads to zeolite materials in the form of nanocrystals free of organic templates, which has excellent adsorption properties with regards to gases, in particular to $O_2$ and $CO_2$ while being biocompatible to make them useful in therapy, more particularly in cancer therapy and hypoxia-related diseases and/or in diagnosis in particular diagnosis of tumors, more particularly of brain tumors.

A first object of the present invention is thus a method for the preparation of a colloidal aqueous suspension of stable zeolite single nanocrystals with monodisperse particle size distribution ranging from about 5 to 200 nm, preferably from about 10 to about 50 nm, and more preferably from about 10 to 25 nm, said stable zeolite single nanocrystals having a three-dimensional framework comprising silicon or silicon and aluminum, said framework comprising channels and cavities at least partially fulfilled with a gas selected from $O_2$, $CO_2$ and mixtures thereof and at least one cation C selected from the group consisting of Gd, Fe, Cu, and Ce in an amount ranging from about 0.1 to about 10 weight % with respect to the total mass of said nanocrystals, wherein said method comprises the following steps:

1) submitting a colloidal suspension CS1 of at least one type stable zeolite nanocrystals with monodisperse particle size distribution ranging from about 5 to 200 nm, preferably from about 10 to about 50 nm, and more preferably from about 10 to 25 nm, said stable zeolite single nanocrystals having a three-dimensional framework comprising silicon or silicon and aluminum, said framework comprising channels and cavities and alkali metal cations M, to an ion exchange of at least a part of the alkali metal cations M with at least one cation C selected from the group comprising Fe, Gd, Cu, and Ce cations, to obtain a colloidal suspension in water CS2 of zeolite single nanocrystals having a three-dimensional framework comprising channels and cavities, and at least one cation C selected from the group comprising Fe, Gd, Cu, and Ce cations in an amount ranging from 0.1 to 10 weight % with respect to the total mass of the zeolite single nanocrystals; and 2) purifying the colloidal suspension CS2 of zeolite single nanocrystals obtained in step 1) with water until a pH ranging from 6.5 to 7.5 is reached; and 3) contacting the purified colloidal suspension of zeolite single nanocrystals obtained in step 2) with at least one gas selected from $O_2$, $CO_2$ and a mixture of $O_2$ and $CO_2$.

Within the meaning of the present invention, the term "clear aqueous suspension" is understood to mean an aqueous suspension having approximately the same refractive index as water, that is to say a refractive index of about $1.333 \pm 0.030$.

Within the meaning of the present invention, the term "nanocrystals with monodisperse particle size distribution" is understood to mean single nanocrystals having approximately the same size and shape.

The process of the present invention, displays high hydrophilicity and high adsorption/desorption properties with regards to different gases, in particular $O_2$ and $CO_2$. Indeed, the process of the invention allows stabilization of the nanocrystals in water suspensions at neutral pH, incorporation of cations C (selected from the group comprising Fe, Gd, Cu and Ce cations), by post synthesis ion exchange, therefore leading to stable synthetic zeolite material displaying excellent colloidal stabilities as well as superior adsorption/desorption properties with regards to different gases in particular $O_2$ and $CO_2$ that makes them particularly useful in therapy, more particularly in cancer therapy and hypoxia-related diseases and/or in diagnosis. They are well suited to improve tumoral tissue oxygenation and/or blood supply. As shown in the examples, the inventors have demonstrated that following intravenous (IV) administration, this zeolite material can leave the blood to enter the brain tumor and release the desired gas (for example $O_2$ or a mixture of $O_2$ and $CO_2$) so as to improve either oxygen concentration or blood volume. This property is particularly interesting in combined treatments to increase tumor sensitivity to radiotherapy. This zeolite material can also be tracked with biomedical imaging such as MRI when the incorporated cation C is Gd or Fe. Therefore, in that case, the zeolite material according to the invention in which the incorporated cation C is Gd or Fe has the supplemental advantage of being usable as contrast agent in imaging, in particular MRI, and is therefore particularly useful for therapies including both diagnosis and treatment called "theranostic".

Within the meaning of the present invention, the term "stable single nanocrystals" is understood to mean nanocrystals free of organic molecules, thus resulting in zeolite nanocrystals having approximately the same size and shape at neutral pH of 7 and from which the incorporated cations C do not leach.

Moreover, the starting materials used in the synthesis are those commonly used in the commercial production of zeolites.

Step 1)

Step 1) of ion exchange can be carried out by adding to the colloidal suspension CS1 a solution containing at least one salt of a cation C selected from the group consisting of Fe, Gd, Cu, and Ce cations, the concentration of said salt of the cation C being such that after addition into the colloidal suspension CS1, the amount of said cation C ranges from about 0.1 to about weight % with respect to the total mass of the zeolite single nanocrystals. Thus, only a part of the alkali metal cation M is replaced with at least one cation C.

According to a preferred embodiment of the present invention, the amount of cation C ranges from about 1 to 5 weight % with respect to the total amount of the zeolite single nanocrystals, and even more preferably from about 1.7 to about 1.9 weight % with respect to the total amount of the zeolite single nanocrystals.

According to an embodiment of the present invention, the concentration of the salt of cation C in the solution that is added into the suspension CS1 may range from about 1 to about 10 mM and more preferably from about 2 to about 6 M.

The salts of cations C may be chosen among hydrated nitrates of formula (I): $C(NO_3)_3.nH_2O$); where C=Gd, Fe, Ce or Cu. Among these nitrates of formula (I), mention may be made in particular of hydrated iron nitrate and hydrated gadolinium nitrate.

According to a particular and preferred embodiment of the present invention, the zeolite single nanocrystals present in the colloidal suspension CS1 are selected from the group comprising:

zeolite single nanocrystals having a FAU- or an EMT-three dimensional framework of $SiO_2$ and $Al_2O_3$ tetrahedra;
zeolite single nanocrystals having an MFI-three-dimensional framework of $SiO_2$ tetrahedra; and
zeolite single nanocrystals having an LTL-three-dimensional framework of $SiO_2$ and $Al_2O_3$ tetrahedra.

Zeolite single nanocrystals having a FAU-three-dimensional framework may have the following molar composition MC1:

9-7 $Na_2O$: 0.7-0.45 $Al_2O_3$: $10SiO_2$: 120-230 $H_2O$

Such zeolites are for example described in international application WO 2016/0325271.

Zeolite single nanocrystals having an EMT-three-dimensional framework may have preferably the following molar composition MC2:

18.45-15 $Na_2O$: 1-0.8 $Al_2O_3$: 5.15-4.0 $SiO_2$: 240-180 $H_2O$, such as those described by E. P. Ng, D. Chateigner, T. Bein, V. Valtchev, S. Mintova, in Science, 335 (2012) 70-73.

Zeolite single nanocrystals having an MFI-three-dimensional framework may have preferably the following molar composition MC3:

1.0-0.7 $SiO_2$: 0.12-0.24 $(TPA)_2O$: 20-100 $H_2O$ wherein, TPA means tetra-n-propylammonium, such as those described by S. Mintova, N. H. Olson, J. Senker, T. Bein "Mechanism of the transformation of silica precursor solutions into Si-MFI zeolite" Angewandte Chemie (2002) 41, 2558-2561.

Zeolite single nanocrystals having an LTL-three-dimensional framework may have preferably the following molar composition MC4:

5 $K_2O$: 10 $SiO_2$: 0.5 $Al_2O_3$: 200 $H_2O$, such as those described for example by A. Kharchenko, O. I. Lebedev, V. Zholobenko, V. de Waele, S. Mintova "Formation of copper nanoparticles in LTL nanosized zeolite: Kinetics study" in J. Phys. Chem. 20 (2016) 26300-26308.

According to the invention, the zeolite single nanocrystals present in the colloidal suspension CS1 used in step 1) has a FAU-type or an EMT-type three-dimensional framework.

Step 1) is preferably carried out under stirring.

At the end of step 1), the colloidal suspension CS2 is preferably kept under stirring at room temperature for about 1 hours before being purified at step 2).

Step 2) is preferably a washing step by double distilled water. This procedure can be repeated several times, in particular three times, until the desired value of pH (neutral) is reached.

According to a preferred embodiment, Step 2) is repeated until the pH of the colloidal suspension CS2 reaches a value of 7±0.2.

After step 2), i.e. during step 3), the zeolite single nanocrystals present in the colloidal suspension CS2 are loaded with a gas selected from $O_2$, $CO_2$ and one of their mixtures, in particular a mixture composed of about 95% by volume of $O_2$ and of about 5% by volume of $CO_2$ (such a particular mixture is named "carbogen").

According to a preferred embodiment of the invention, step 3) is performed by bubbling the colloidal suspension CS2 with pure $O_2$, pure $CO_2$ or with a mixture composed of about 95% by volume of $O_2$ and of about 5% by volume of $CO_2$.

The bubbling of the colloidal suspension CS2 can be made for example at a flow rate of 70 to 90 mL/min for 15 to 60 minutes. According to a particularly preferred embodiment of the present invention, the bubbling of the colloidal suspension CS2 is carried out at a flow rate of about 80 mL/min for about 30 min.

After step 3) said zeolite single nanocrystals can be directly used in therapy, more particularly in cancer therapy and hypoxia-related diseases and/or in diagnosis.

According to a preferred embodiment of the present invention, the colloidal suspension CS1 used during step 1) can be prepared according to the process described in international application WO 2015/101800, said process comprising the following steps:

i) separately preparing a clear aqueous aluminate suspension A comprising at least one source of aluminum and at least one source of at least one alkali metal cation M, and a clear aqueous silicate suspension B comprising at least one source of silicon and at least one source of at least one alkali metal cation M;

ii) admixing the clear aqueous aluminate suspension A and the clear aqueous suspension B until a resulting aqueous suspension is obtained, said resulting aqueous suspension being free of organic templating agent and having a molar composition MC1, MC2, MC3 or MC4, as described hereabove;

iii) aging the resulting suspension of step ii) at a temperature ranging from about 20° C. to about 30° C. to form nuclei;

iv) heating the resulting suspension of step iii) at a temperature of 40, 60, 90, 100 or 170° C., for a period of time sufficient to produce the colloidal suspension CS1, in particular a colloidal suspension of zeolite single nanocrystals having a FAU-, an EMT-, a LTL- or an MFI-three-dimensional framework of $SiO_4$ and $AlO_4$ tetrahedra encompassing channels and cavities, wherein said framework comprises at least one alkali metal cation M.

Step i):

The source of aluminum can be selected from any source of aluminum that is able to provide monomeric oxyhydroxide species. Within the meaning of the present invention, the term "any source of aluminum that is able to provide monomeric oxyhydroxide species" is understood to mean that this source of aluminum does not provide polymeric aluminum oxyhydroxide species and allows all the aluminum to be dissolved in the clear aqueous suspension A [R. M. Barrer, "Hydrothermal Chemistry of Zeolites", 1982, Academic Press, London].

In particular, the source of the aluminum can be selected from alumina, hydrated alumina, aluminum powder, $AlCl_3$, $Al_2(SO_4)_2$, aluminum hydroxide $Al(OH)_3$, sodium aluminate and kaolin clays.

Sodium aluminate is preferred.

The source of silicon can be selected from any source of silicon that is able to provide during step i) monomeric or $Si_2$-$Si_6$ oxyhydroxide species. Thus, the amount of larger $[SiOOH]_n$ units is limited in the clear aqueous suspension B [R. M. Barrer, "Hydrothermal Chemistry of Zeolites", 1982, Academic press, London].

In particular, the source of silicon can be selected from silica hydrogel, silicic acid, colloidal silica, fumed silica, tetraalkyl orthosilicates, silica hydroxides, precipitated silica and clays.

Colloidal silica is preferred.

The source of alkali metal M can be selected from a source of Na and a source of K. A source of Na such as NaOH is preferred, while for K the hydroxide (KOH) is used.

Step ii)

Preferably, the admixing step ii) is performed at a temperature going from 0° C. to 20° C. approximately, and preferably going from 0° C. to 5° C. approximately. These conditions help to better decrease the polymerization kinetics between silica and alumina based-species and obtain highly uniform amorphous particles (in chemical composition and particle size) in the resulting suspension.

In a preferred embodiment, the clear aqueous aluminate suspension A is added drop wise to the clear aqueous silicate suspension B, said clear aqueous silicate suspension B being kept at a temperature going from 0° C. to 20° C., and more preferably going from 0° to 5° C.

It is also preferable to have the clear aqueous aluminate suspension A and the clear aqueous silicate suspension B mix under vigorous mechanical stirring or sonication, preferably during about 10 minutes to about 1 h.

Step iii):

Preferably, the resulting aqueous suspension obtained in step ii) is maintained from about 21° C. to about 27° C. This temperature should be maintained for a time sufficient to favor the nucleation. Thus, during the aging process each particle can generate a nucleus.

Preferably, the temperature of the aging step iii) is maintained for at least 12 hours approximately, preferably for 20 hours approximately, and more preferably for 1 day approximately.

The ageing step iii) is generally performed without any agitation (i.e. without any mechanical stirring or any sonication).

Thanks to steps ii) and iii), uniformity is reached on the size of the amorphous nanoparticles in the resulting suspension.

Step iv):

During step iv), nuclei formed at the preceding step iii) grow to form single nanocrystals, thus leading to uniform single nanocrystals with a size controllable by the method conditions.

Step iv) is preferably performed at atmospheric pressure until the single nanocrystals of synthetic zeolite material are formed.

The crystallization time required to form single nanocrystals will typically range from about 30 minutes to about 4 days, and more frequently from about 40 min to about 2.5 days.

Step iv) is preferably performed in the absence of seed crystals added prior to step iv).

Step iv) is generally performed without any agitation (i.e. without any mechanical stirring or any sonication).

According to a particulate embodiment of the present invention, the method may further comprise, after Step iv) and before Step 1) of the main process, an intermediate Step iv') of purifying the nanocrystals obtained at the end of Step iv). This intermediate step iv') of purifying may for example be performed by submitting the dispersion of nanocrystals to several cycles of centrifugation/redispersion in distilled water, preferably until the pH of the redispersion reaches a value of about 8.5.

A second object of the present invention is the colloidal aqueous suspension of a zeolite material prepared according to the method as defined in the first object of the present invention, wherein:

said zeolite material is the form of stable zeolite single nanocrystals with monodisperse particle size distribution ranging from about 5 to 200 nm, preferably from about 10 to about 50 nm, and more preferably from about 10 to 25 nm, said stable zeolite single nanocrystals has a three-dimensional framework comprising silicon or silicon and aluminum, said framework comprising channels and cavities at least partially fulfilled with a gas selected from $O_2$, $CO_2$ and mixtures thereof, and said framework comprises at least one cation C selected from the group comprising Fe, Gd, Cu, and Ce in an amount ranging from about 0.1 to about weight % with respect to the total mass of said nanocrystals.

According to a preferred embodiment of the present invention, the amount of cation C ranges from about 1 to 5 weight % with respect to the total mass of said nanocrystals, and even more preferably from about 1.7 to about 1.9 weight % with respect to the total mass of said nanocrystals.

In one embodiment, said zeolite material has a specific surface area $S_{BET}$ ranging from about 250 to 930 $m^2 \cdot g^{-1}$, and preferably from about 450 to 850 $m^2 \cdot g^{-1}$.

The zeolite material of the present invention can have a total pore volume $V_{total}$ ranging from about 0.12 to 1.6 $cm^3 \cdot g^{-1}$, and preferably from about 0.8 to 1.2 $cm^3 \cdot g^{-1}$.

The zeolite material of the present invention can have an external surface area $S_{ext}$ ranging from about 20 to 190 $m^2 \cdot g^{-1}$, and preferably from about to 140 $m^2 \cdot g^{-1}$.

Among the mentioned cations C, Gd, Fe, and a mixture of Gd and Fe are most preferred.

In a first preferred particular embodiment of the present invention, said cation C is Gd and the amount of Gd ranges from about 1.2 to about 1.9% by mass with respect to the total mass of the zeolite material.

In a second preferred particular embodiment of the present invention, said cation is Fe and the amount of Fe ranges from about 0.9 to about 2% by mass with respect to the total mass of the zeolite material.

In a third preferred particular embodiment of the present invention, the zeolite material comprises a mixture of cations Gd and Fe and the amount of Gd ranges from about 1 to about 5% by mass with respect to the total mass of the synthetic zeolite material and the amount of Fe ranges from about 0.9 to about 2% by mass with respect to the total mass of the zeolite material.

According to a particularly preferred embodiment of the invention, the colloidal suspension comprises a zeolite material Gd—Fe-ZM containing 3.33% by mass of Gd and 0.06% by mass of Fe with respect to the total mass of the defect-free synthetic zeolite material Gd—Fe-ZM and has a mean dimension ranging from about 10 to 30 nm.

As explained here before, the zeolite material of the present invention has the ability of desorb gas it contains to a surrounding media deprive of such a gas.

A third object of the present invention is a colloidal aqueous suspension of a zeolite material as prepared according to the method as defined in the first object of the present invention or as defined in the second object of the present invention for use in therapy, in particular in cancer therapy, or for the treatment of hypoxia-related diseases, and/or in diagnosis, in particular diagnosis of tumors, more particularly of brain tumors.

A fourth object of the present invention, is a colloidal aqueous suspension of a zeolite material, as prepared according to the method as defined in the first object of the present invention or as defined in the second object of the present invention, for its use as a contrast agent in imaging, in particular MRI.

A fifth object of the present invention is a pharmaceutical composition comprising at least one colloidal aqueous suspension of a zeolite material as prepared according to the method as defined in the first object of the present invention or as defined in the second object of the present invention, together with a pharmaceutical carrier.

According to a preferred embodiment of the present invention, said pharmaceutical composition is an injectable composition, in particular an intravenous injectable composition.

In said pharmaceutical composition, the amount of the at least one said zeolite material may range from about 1 to 14% by mass, preferably from about 2 to 9% by mass, with regard to the total mass of said composition.

The pharmaceutical carrier may be selected from all carriers compatible with an administration to the human body, in particular by intravenous injection, such a physiological serum or water for injection.

This pharmaceutical composition is indicated in the treatment of cancers, in particular brain tumors and also in the treatment of hypoxia-related diseases. This pharmaceutical composition can advantageously be administered before a radiotherapy treatment to increase the sensitivity of tumors to radiation therapy.

This pharmaceutical composition may further comprise one or several therapeutic agents, such as those usually present in pharmaceutical compositions indicated in the treatment of cancers. Mention may be made in particular of chemotherapies.

Finally, a sixth object of the present invention is a diagnosis composition comprising at least one colloidal aqueous suspension of a zeolite material as prepared according to the method as defined in the first object of the present invention or as defined in the second object of the present invention, together with a biocompatible carrier.

In a preferred embodiment, the diagnostic composition is an imaging composition, in particular an MRI diagnosis composition.

In said diagnosis composition, the amount of the at least one said zeolite material may range from about 0.01 to 3% by mass, preferably from about 1 to 3% by mass, with regard to the total mass of said composition. The amount may range from about 1 to 3 ml/Kg body weight in rodents.

The biocompatible carrier be selected from all carriers compatible with an administration to the human body, in particular by intravenous injection, such a physiological serum or water for injection.

EXAMPLES

Figure 1:
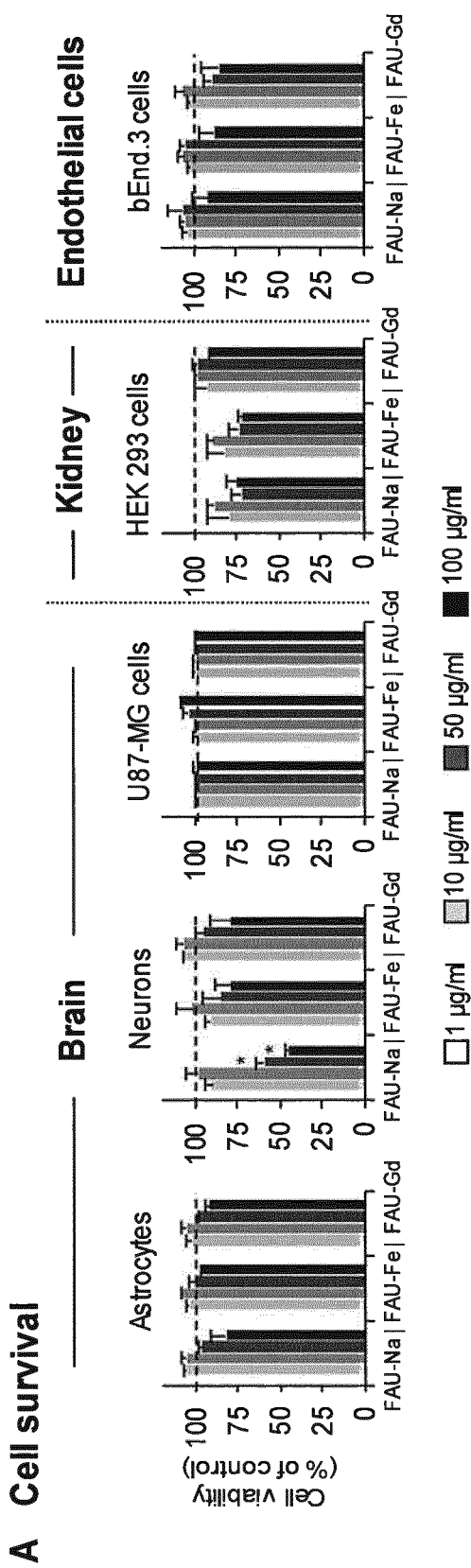
FIG. 1 represents (A) the results of quantification of astrocytes, neurons, U87-MG, HEK 293 and bEnd.3 cells viability following a 48 h exposure to increasing concentrations of FAU-Na, FAU-Gd or FAU-Fe; (B) the result of effect of nanosized zeolites on the cell cycle on U87-MG and HEK 293 cells, assessed using flow cytometry after exposure to 100 µg/ml of FAU-Na, FAU-Gd, FAU-Fe or water as a control for 14 h and 48 h.
Figure 1:
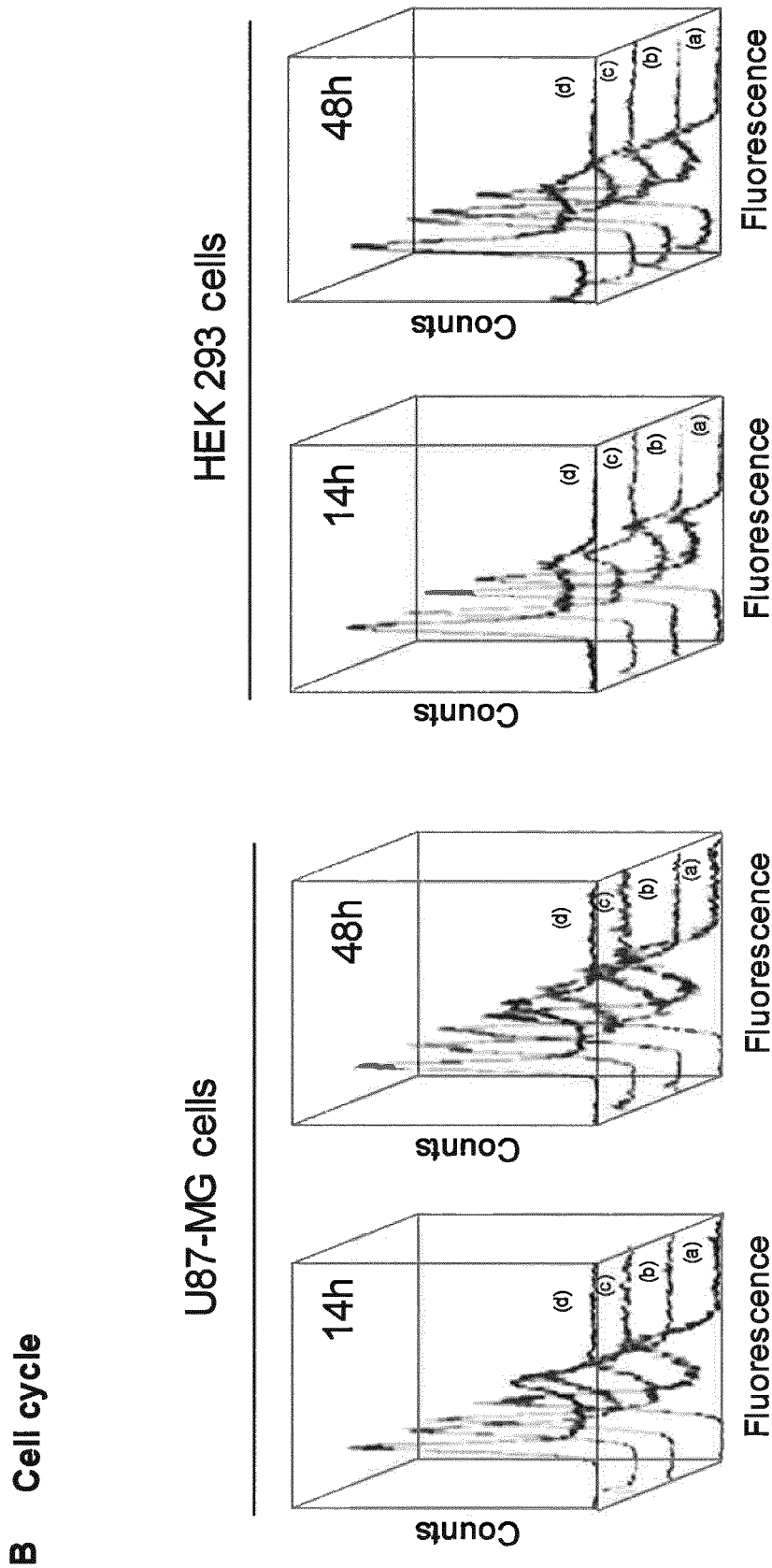

The starting materials used in the examples which follow, are listed below:
   sodium aluminate ($NaAlO_2$) (Strem-chemicals, 56.7% $Al_2O_3$, 39.5% $Na_2O$);
   sodium hydroxide (NaOH): Sigma Aldrich;
   colloidal silica (Ludox-HS 30, 30 wt % $SiO_2$, pH=9.8): Aldrich;
   iron nitrate ($Fe(NO_3)_3.9H_2O$) (Aldrich, 99.9%);
   gadolinium nitrate hexahydrate ($Gd(NO_3)_3.6H_2O$);
   sodium silicate ($Na_2SiO_3$) (Prolabo, 29% $SiO_2$, 8% $Na_2O$)
   aluminum powder (325 mesh, 99.5% purity): Alfa Aesar;
These starting materials were used as received from the manufacturers, without additional purification.

The various zeolite material obtained in the examples were characterized over various scales of sizes.

Transmission Electron Microscopy (TEM):

Diluted colloidal suspensions of zeolite material obtained after step 3) were sonicated for 15 min and then 2-3 drops of fine particle suspensions were dried on carbon-film-covered 300-mesh copper electron microscope grids. The crystal size, morphology and crystallinity of solids were determined by a transmission electron microscopy (TEM) using a JEOL 2010 FEG operating at 200 kV.

Dynamic Light Scattering (DLS) Analysis:

The hydrodynamic diameters of the zeolite material in the various suspensions were determined with a Malvern Zetasizer Nano. The analyses were performed on samples after purification with a solid concentration of 10 wt % and pH=8. The back-scattering geometry (scattering angle 173°, HeNe laser with 3 mW output power at 632.8 nm wavelength) allows measurements at high sample concentration, since a complete penetration of the incident light through the sample is not required.

Example 1: Preparation of a Colloidal Aqueous Suspension of Single Nanocrystals Having a FAU Type Tetrahedral Framework Comprising Fe as Cation C A colloidal aqueous suspension CS1-1 was first prepared according to the following steps i) to iv'):

Step i)

A clear aqueous aluminate suspension A was prepared by dissolving 0.92 g of sodium aluminate in 3 g of double-distilled (dd) $H_2O$ (water clear within 2-3 min).

A clear aqueous silicate suspension B was prepared by mixing 10 g of colloidal silica with 3.37 g of NaOH, and 1 g of dd $H_2O$. As a result, a turbid suspension was obtained. In order to transform the turbid suspension into a clear suspension, the turbid suspension was stirred well for 1-2 min, or placed on a shaker for 1 min.

Step ii):

Solution A was added spontaneously under stirring to the solution B; during the mixing, solution B was kept in ice, as a result semi-transparent viscous precursor suspension was obtained, and transformed into a water clear suspension during the first 1-2 hours of aging time.

The resulting clear suspension had the following molar composition: $8.5Na_2O: 1.1Al_2O_3: 10SiO_2: 122H_2O$.

Step iii):

The resulting clear suspension was then aged 24 h at room temperature (i.e. 25° C.), dehydrated under vacuum, and the water content was adjusted to the following molar composition.

$8.5Na_2O: 1.1Al_2O_3: 10SiO_2: 50H_2O$.

Step iv):

Then, the hydrothermal crystallization was conducted at 50° C. for 1 day to obtain monodisperse nanoparticles of a synthetic faujasite material dispersed in mother liquor, said nanoparticles having a particle size of 10 nm.

Steps iv'):

Single nanocrystals of the synthetic faujasite material were purified by three steps centrifugation (25.000 rpm for 4 h) followed by redispersion in water until reached pH=8.5 and with a content of 5 wt. % of zeolite with respect to the total mass of the dispersion.

The Si/Al molar ratio of the obtained synthetic faujasite material was 1.03, with a Si concentration of 71.43 mg/l, an Al concentration of 67.56 mg/l, and a Na concentration of 60.32 mg/l.

The resulting colloidal aqueous suspension CS1-1 obtained after step iv') above, was then used in the following steps 1 to 3).

Step 1)

20 ml $Fe(NO_3)_3.9H_2O$ with a concentration in the range of $5.0-5.1.10^{-5}M$ was added to 20 ml of the zeolite suspension obtained in step iv') (5 wt. % zeolite) and kept for 1 h.

Step 2)

The zeolite was purified by one cycle centrifugation and redispersion in distilled water. The procedure was repeated two or three times. The final ion-exchanged samples were purified three times with distilled $H_2O$ by consecutive high-speed centrifugation and redispersion in distilled water until the pH value reached 7.

Step 3)

The purified colloidal aqueous suspension obtained in step 2) was then bubbled with $O_2$ or $CO_2$ or carbogen at a flow rate of 80 mL/min for 30 minutes.

Characterizations

The as synthesized FAU nanocrystals comprising Fe as cation C (FAU-Fe) obtained at the end of step 2) have then been characterized. The main characteristics of the FAU-Fe material thus obtained, including the dynamic diameter obtained by DLS analysis of the suspension prior step 3) are given in Table 1 below:

TABLE 1

| Chemical composition (wt. %) | | | | Diameter | Zeta Potential |
| --- | --- | --- | --- | --- | --- |
| Si | Al | Na | Fe | (nm) | (mV) |
| 46.07 | 39.05 | 13.18 | 1.71 | 10-30 | −37.7 |

As a reference for comparative purpose in the following example, FAU nanocrystals not forming part of the present invention, i.e. not comprising any cation C have also been prepared according to the same process until step iv'), i.e. the step 1) of ion-exchange was not performed (FAU-Na).

These FAU-Na nanocrystals had the characteristics given in Table 2 below:

TABLE 2

| Chemical composition (wt. %) | | | | | Diameter | Zeta Potential |
|---|---|---|---|---|---|---|
| Si | Al | Na | Fe | Gd | (nm) | (mV) |
| 40.05 | 32.66 | 27.21 | 0.0 | 0.0 | 10-30 | −37.7 |

Example 2: Preparation of a Colloidal Aqueous Suspension of Single Nanocrystals Having a FAU Type Tetrahedral Framework Comprising Gd as Cation C A colloidal aqueous suspension CS2-2 of single nanocrystals having a FAU type tetrahedral framework comprising Gd as cation C was prepared according to the same process as detailed in example 1 above until step iv') included.

The colloidal aqueous suspension CS1-1 obtained after step iv') above, was used in the following steps 1 to 3).

Step 1)

The as-prepared zeolite suspension CS1-1 obtained in step iv') of example 1 was ion-exchanged by gadolinium (III) nitrate hexahydrate (Gd(NO$_3$)$_3$.6H$_2$O).

25 mL of Gd(NO$_3$)$_3$.6H$_2$O (3 mM) were added on 5 mL of said suspension (2.5%). The suspension was then kept under stirring at room temperature for 1 h.

Step 2)

The suspension was washed by double distilled water. This procedure was repeating three times to obtain finally a suspension CS2-2 of FAU-Gd zeolite having a pH of 7.

Step 3)

The purified colloidal aqueous suspension obtained in step 2) was then bubbled with O$_2$ or CO$_2$ or carbogen at a flow rate of 80 mL/min for 30 minutes.

Characterizations

The as synthesized FAU nanocrystals comprising Gd as cation C (FAU-Gd) obtained at the end of step 2) have then been characterized. The main characteristics of the FAU-Gd material thus obtained, including the dynamic diameter of zeolite nanocrystals obtained by DLS analysis of the suspension prior to step 3) and chemical analysis by ICP are given in Table 3 below:

TABLE 3

| Chemical composition (wt. %) | | | | Diameter | Zeta Potential |
|---|---|---|---|---|---|
| Si | Al | Na | Gd | (nm) | (mV) |
| 44.70 | 33.85 | 18.06 | 3.33 | 10-30 | −37.7 |

Example 3: Preparation of a Colloidal Aqueous Suspension of Single Nanocrystals Having an EMT Type Tetrahedral Framework Comprising Fe as Cation C A colloidal aqueous suspension CS2-3 of single nanocrystals having an EMT type tetrahedral framework comprising Fe as cation C has been prepared according to the same process as in example 1 above until step iv'), except that during step iii) the aging was performed at 23° C. for 14 h and during step iv), the hydrothermal crystallization was conducted at 30° C. for 36 hours.

The precursor suspension had the following molar composition: 5SiO$_2$:1Al$_2$O$_3$:17.48Na$_2$O:340.3H$_2$O (9.074 g NaAlO$_2$, 65.610 g NaOH, 57.693 g Na$_2$SiO$_3$, 180 g H$_2$O).

The colloidal aqueous suspension CS1-3 obtained after step iv') above, was used in the following steps 1 to 3).

Step 1)

20 ml Fe(NO$_3$)$_3$.9H$_2$O with a concentration in the range of 5.0-5.1.10$^{-5}$M was added to 20 ml of the EMT zeolite suspension obtained in step 4') (5 wt. % zeolite) and kept for 1 h.

Step 2)

The zeolite was purified by one cycle centrifugation and redispersion in distilled water. The procedure was repeated two or three times. The final ion-exchanged samples were purified three times with distilled H$_2$O by consecutive high-speed centrifugation and redispersion in distilled water until the pH value reached 7.

Step 3)

The purified colloidal aqueous suspension obtained in step 2) was then bubbled with O$_2$ or CO$_2$ or carbogen at a flow rate of 80 mL/min for 30 minutes.

Characterizations

The as synthesized EMT nanocrystals comprising Fe as cation C (EMT-Fe) obtained at the end of step 2) have then been characterized. The main characteristics of the EMT-Fe material thus obtained, including the dynamic diameter obtained by DLS analysis of the suspension prior to step 3) are given in Table 4 below:

TABLE 4

| Chemical composition (wt. %) | | | | Diameter | Zeta Potential |
|---|---|---|---|---|---|
| Si | Al | Na | Fe | (nm) | (mV) |
| 35.9 | 34.7 | 11.5 | 2.8 | 15-50 | −37.0 |

Example 4: Preparation of a Colloidal Aqueous Suspension of Single Nanocrystals Having an EMT Type Tetrahedral Framework Comprising Gd as Cation C A colloidal aqueous suspension CS2-4 of single nanocrystals having an EMT type tetrahedral framework comprising Gd as cation C was prepared according to the same process as detailed in example 3 above until step iv') included.

The colloidal aqueous suspension CS1-3 obtained after step iv') above, was used in the following steps 1 to 3).

Step 1)

The as-prepared zeolite suspension CS1-3 obtained in step iv') of example 3 was ion-exchanged by gadolinium (III) nitrate hexahydrate (Gd(NO$_3$)$_3$.6H$_2$O).

25 mL of Gd(NO$_3$)$_3$.6H$_2$O (3 mM) were added on 5 mL of said suspension (2.5%). The solution was then kept under stirring at room temperature for 1 h.

Step 2)

The zeolite was then washed by double distilled water. This procedure was repeating three times to obtain finally the suspension of EMT-Gd zeolite at a pH 7.

Step 3)

The purified colloidal aqueous suspension obtained in step 2) was then bubbled with O$_2$ or CO$_2$ or carbogen at a flow rate of 80 mL/min for 30 minutes.

Characterizations

The as synthesized EMT nanocrystals comprising Gd as cation C (EMT-Gd) obtained at the end of step 2) have then been characterized. The main characteristics of the EMT-Gd material thus obtained, including the dynamic diameter obtained by DLS analysis of the suspension prior to step 2) are given in Table 5 below:

TABLE 5

| Chemical composition (wt. %) | | | | Diameter | Zeta Potential |
|---|---|---|---|---|---|
| Si | Al | Na | Gd | (nm) | (mV) |
| 35.8 | 34.3 | 10.9 | 1.8 | 15-50 | −36.6 |

Example 5: In Vitro Verification of the Innocuity of the Nanosized Zeolite Material of the Invention 5.1. Materials and Methods Multiple cell types originating from various organs were exposed to nanosized zeolites. Both pathological and healthy brain cells were used: mouse brain endothelial cells (bEnd.3 cell line), mouse astrocytes and neurons (primary culture), and human glioma cells (U87-MG) and a cell type derived from the kidney (HEK 293 cell line), as follows:

Cell Lines

A human glioblastoma cell lines, U87-MG purchased from American Type Culture Collections (ATCC, Manassas, Va., USA) and HEK 293 cells (Human Embryonic Kidney cells) were used. Cells were cultured in DMEM (Sigma-Aldrich, France) supplemented with 10% fetal bovine serum (Eurobio, France), 2 mM glutamine (Sigma-Aldrich, France) and penicillin (1000 U/ml)/streptomycin (100 μg/ml)(Sigma-Aldrich, France).

bEnd.3 mouse brain endothelial cells were purchased from ATCC and cultured in high glucose (4500 mg/l) DMEM (Sigma-Aldrich, France) supplemented with 10% fetal bovine serum (Eurobio, France), 2 mM glutamine (Sigma-Aldrich, France) and penicillin (1000 U/ml)/streptomycin (100 μg/ml) (Sigma-Aldrich, France). Cells were maintained in culture at 37° C. with 5% $CO_2$ and 95% humidity.

Primary Culture of Astrocytes

Cerebral cortices were isolated from neonatal (1 to 3-day-old) mice (Swiss, CURB, France) carefully stripped of the meninges and dissociated to generate a single-cell suspension. Cultures were allowed to grow in a humidified 5% $CO_2$ incubator at 37° C. to confluency (15-20 days) prior to use in DMEM supplemented with 10% fetal bovine serum (Eurobio, France), 10% horse serum (Eurobio, France), 2 mM glutamine (Sigma-Aldrich, France) and penicillin (1000 U/ml)/streptomycin (100 μg/ml) (Sigma-Aldrich, France). At about 80% confluence, the growth medium was replaced by the same medium.

Primary Cultures of Cortical Neurons/Astrocytes

Cultures were prepared from E15-E16 mouse embryos (Swiss mice; CURB, France). Microdissection of cortices was followed by a dissociation of the tissue in a 37° C. DMEM (Sigma-Aldrich, France). Cells grew on plates coated with poly-d-lysine (0.1 mg/ml) and laminin (0.02 mg/ml) in DMEM supplemented with 5% fetal bovine serum, 5% horse serum (Eurobio, France), and 2 mM glutamine (Sigma-Aldrich, France). Cells were maintained in a humidified 5% $CO_2$ atmosphere at 37° C. Neurons were used after 12 d in vitro.

Cells Exposure to Nanosized Zeolites

Cells were exposed to zeolites (FAU-Na as prepared in example 1 used as a reference not forming part of the present invention, FAU-Fe and FAU-Gd as prepared also according to example 1 but forming part of the present invention) for various times. Zeolites were diluted in culture medium at a concentration of 1, 10, 50 or 100 μg/ml and added directly into the wells. The control condition consisted of an addition of pure water only into the wells with the same volume as for zeolites solutions.

Cells Viability

Cells were seeded in 24-wells plates to achieve 80% confluency for the control on the day of the analysis. Cell viability was assessed 48 h following exposure to zeolites with the WST-1 assay (Roche, France) according to manufacturer's instructions.

Cell Cycle Analysis

At various time points following cell exposure to 100 μg/ml of nanosized zeolites, cell cycle of U87-MG and HEK 293 cells was studied by flow cytometry with Coulter DNA Prep Reagents kit according to manufacturer's instructions (Beckman Coulter SAS, France). Propidium iodide staining was analyzed using the Beckman Coulter's Gallios flow cytometer (Beckman Coulter SAS, France) with 10 000 events per determination. Analysis and determination of cell distribution in each phase of cell cycle was performed using the Kaluza software (Beckman Coulter SAS, France).

DNA Double Strands Breakdown and Micronuclei Formation Analysis by Immunocytochemistry Cells were plated in 24-well plates on coverslips and one day later were exposed to 100 μg/ml of zeolites for 14, 24 or 48 h. The positive controls consisted of cells 30 min after irradiation with a dose of 4Gy (XRad225Cx, PXi, CYC-ERON platform). Cells were then fixed for 1 h at 4° C. with 4% PFA. Non-specific bindings were blocked with a solution of 3% bovine serum albumin (BSA) (Sigma-Aldrich, France)-PBS-0.1% Tween (Sigma-Aldrich, France) for 1 hour at room temperature. Then, cells were incubated overnight at 4° C. with a primary antibody. The following primary antibodies was used: phospho-histone H2AX (ser139) (1/200; Cell Signaling Technology, D175, 2577S) in 1% BSA-PBS-0.1% Tween. The revelation was achieved by an Alexa-555-conjugated anti-rabbit secondary antibody (1/200; Molecular Probes, A21429). Cells were counter-stained with Hoechst 33342 (10 μg/ml; Sigma-Aldrich, France) for nuclear staining. All immunocytochemistry markers were observed on a Leica DMi8 microscope with a 40× objective. For each condition, at least 3 coverslips were analyzed and images from 5 representative fields per slide were acquired.

5.2. Results

The results of cell survival are reported on FIG. 1 annexed.

FIG. 1A gives the results of quantification of astrocytes, neurons, U87-MG, HEK 293 and bEnd.3 cells viability following a 48 h exposure to increasing concentrations of FAU-Na, FAU-Gd or FAU-Fe. On this figure, the cell viability is given in % of control for each tested concentration. A slight dose-dependent decrease in cell viability following exposure to concentrations exceeding 10 μg/ml for all cell types was observed, except for U87-MG cells for which no change in cell viability was observed whatever the concentration used. Neurons appeared to be the most sensitive cell type since the maximum loss in cell viability (65.8±2.1%) was achieved when exposed to 100 μg/ml of FAU-Na. The presence of gadolinium (FAU-Gd) or the presence of iron (FAU-Fe) did not induce any further toxicity relative to Na whatever the cell type and the concentration used. These data strongly support that a dramatic effect of nanosized zeolites on the cell viability can be excluded.

The result of effect of nanosized zeolites on the cell cycle on U87-MG and HEK 293 cells, assessed using flow cytometry after exposure to 100 μg/ml of FAU-Na, FAU-Gd, FAU-Fe or water as a control for 14 h and 48 h are provided on FIG. 1B annexed. No difference of the cell distribution in the different phases of cell cycle between the control group and cells exposed to nanosized zeolites was noticed (FAU-Na, FAU-Fe or FAU-Gd) for both cell types and for the two exposure times.

Figure 2:
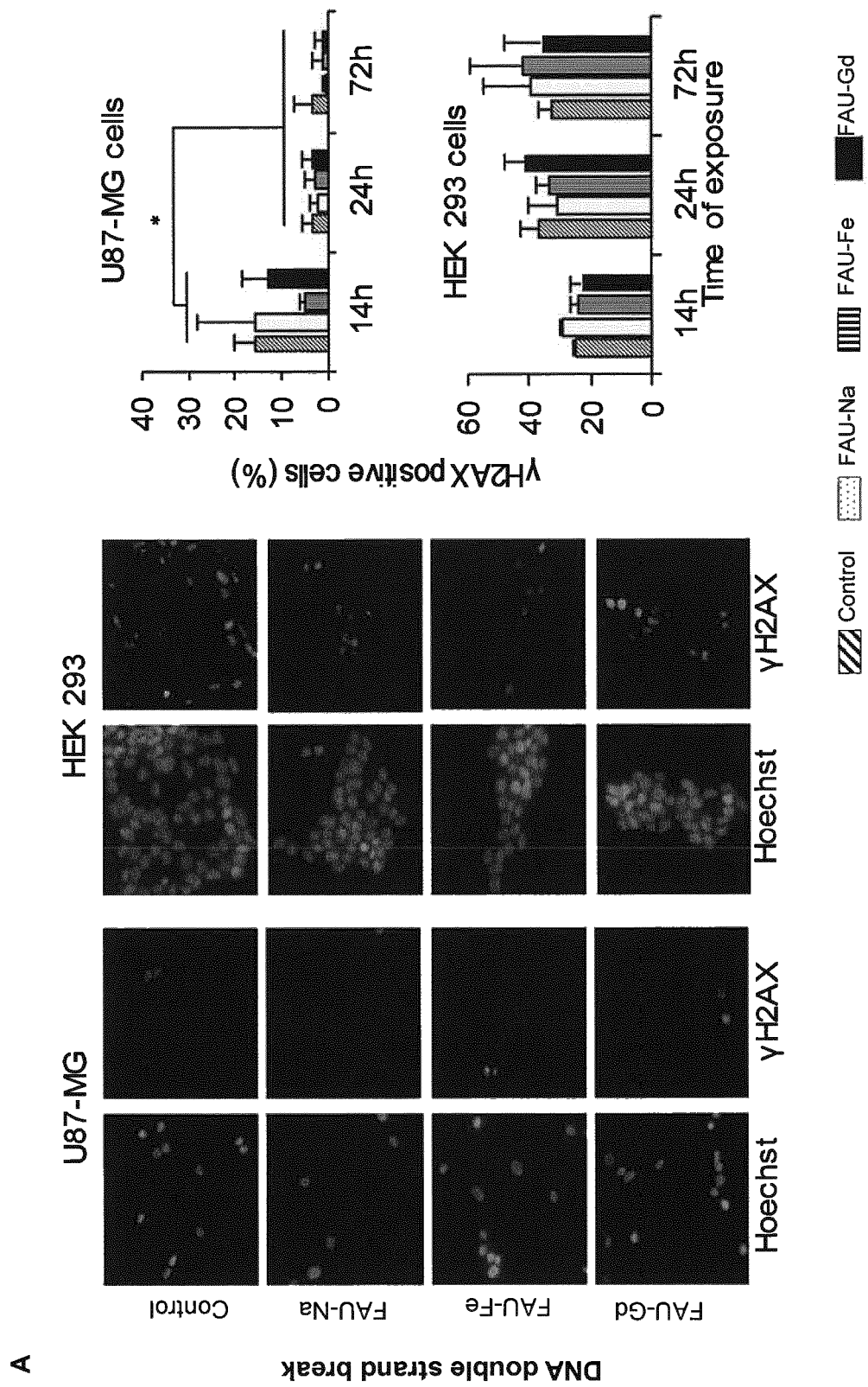
FIG. 2 represents the results of genotoxicity assays. A) γH2AX staining (left panel) and corresponding quantification (right panel) on U87-MG and HEK293 cells after exposure to FAU-Na, FAU-Fe and FAU-Gd at 100 µg/ml for 14 h0, 24 h or 72 h.B) Micronucleus detection after Hoechst 33342 staining (left panel) and corresponding quantification (right panel) on U87-MG and HEK293 cells after exposure to FAU-Na, FAU-Fe and FAU-Gd at 100 µg/ml for 14 h0, 24 h or 72 h.
Figure 2:
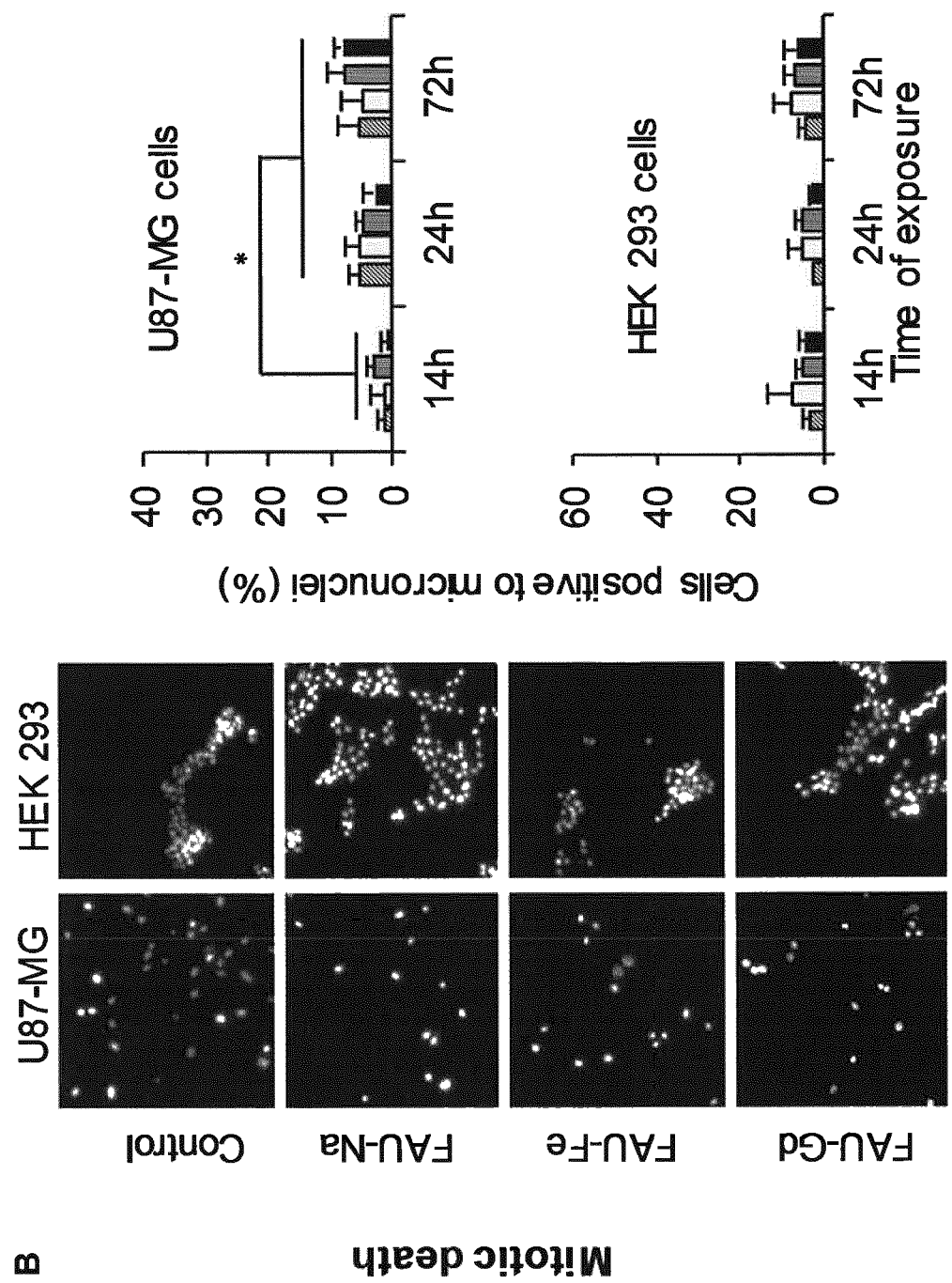

The results of the potential genotoxic effect of nanosized zeolites using immunofluorescent labeling of γH2AX as a marker of DNA double strand breaks and the micronucleus formation assay as a marker of mitotic death are given by FIG. 2 annexed. U87-MG cells showed almost no γH2AX positive cells for control conditions or after exposure to zeolite materials FAU-Na, FAU-Gd or FAU-Fe. A slight decrease in the marker was observed after 24 h of experiment for all conditions. HEK 293 cells exhibited a higher proportion of γH2AX positive cells compared to U87-MG cells and the percentage of γH2AX positive cells slightly increased after 24 and 72 h of experiment. However, no change in the proportion of γH2AX positive cells after exposure to FAU-Na, FAU-Gd or FAU-Fe as compared to the control condition were detected (FIG. 2A). These results are also supported by the micronuclei formation assay. Both for U87-MG and HEK 293 cells, the number of cells forming micronucleus was low (below 10%) whatever the duration of the experiment (FIG. 2B). Furthermore, compared to the control, there is no significant increase in the formation of micronuclei after exposure to FAU-Na and FAU-Gd. As a whole, in term of DNA damages, these results allow to conclude, that FAU-Na, FAU-Fe and FAU-Gd do not have a genotoxic effect.

Overall, these data support for absence of adverse effects of FAU-Na (reference not forming part of the present invention), FAU-Gd and FAU-Fe (nanosized zeolite material according to the invention) in vitro on a wide range of cells type originating from the tumor, the healthy brain, the kidney and the endothelium.

Example 6: Study of the Vasoactive Effect of Nanosized Zeolite Material According to the Invention Carrying $CO_2$ In this example, the vasoactive effect of nanosized zeolite material Gd-FAU as prepared in example 1, carrying $CO_2$ or Carbogen, was studied.

To study the functional benefit of this material as gas carrier, a multiparametric MRI in a rat orthotopic model of glioblastoma was used.

6.1. Materials and Methods

Ethical Approval and Animal Issues

Animal investigations were performed under the current European directive (2010/63/EU) as incorporated in national legislation and in authorized laboratories (B14118001). The animals were obtained from an inhouse breeding stock at the Centre Universitaire de Ressources Biologiques (CURB, A14118015). The male athymic nude rats (250-300 g, three to four months) were maintained in specific pathogen free housing and were fed with γ-irradiated laboratory food and given water ad libitum Animals were manipulated under deep anesthesia (5% isoflurane for induction, 2% for maintenance in 70% $N_2O$/ 30% $O_2$). Body temperature was monitored and maintained at 37.5±0.5° C. with a feedback-controlled heating pad connected to a rectal probe.

Orthotopic Glioma Cells Implantations

U87-MG (ATCC, LGC Standards Molsheim, France) cells were stereotactically injected into the caudatoputamen of rats. Briefly, animals were anesthetized, body temperature was monitored and maintained around 37.5° C. Rats were placed in a stereotactic head holder and a scalp incision was performed along the sagittal suture. A 1 mm diameter burr hole was drilled in the skull. U87-MG cells ($5.10^4$ cells in 3μlPBS-glutamine 2 mM) were injected over 6 min via a fine needle (30G) connected to a Hamilton syringe. The injection site was the right caudatoputamen with stereotactic coordinates: AP=0, L=3 and D=6 mm. The needle was then slowly removed and the craniotomy sealed.

Imaging Experiments

For characterization of tumor, Magnetic Resonance Imaging (MRI) experiments were done once a week. MRI was performed on a 7 teslas horizontal magnet (Pharmascan, Bruker, Ettlingen). A cross coil configuration was used (volume/surface coil, Bruker, Ettlingen). The tumor was detected using an accelerated T2w sequence (RARE, acceleration factor of 8; TR/TEeff=5000/62.5 msec; number of experiments (NEX=2; 20 contiguous slices; resolution=0.15×0.15×0.50 mm3; acquisition time=4 min). Tumor volumes were delineated manually with ImageJ software.

Detection of FAU-Gd with MRI

Experiments were performed on tumor bearing rats on a 7 teslas horizontal magnet (Pharmascan, Bruker, Ettlingen). After a scout view and a T2w-RARE8 scan, 300 μl of a 1% solution of FAU-Gd was administered intravenously and T2*w-EPI (TR/TE=20,000/12 ms, Number of EXcitation: NEX=3, 50 contiguous slices, resolution=0.3×0.3×0.3 mm) or T1w-FLASH images (TR/TEeff=500/10.32 ms; NEX=1; 10 slices; resolution=0.15×0.15×1.5 mm3; acquisition time=2 min) were obtained prior to and every 2 min following the injection.

Relaxometry

FAU-Gd nanocrystals were dissolved in distilled water in concentration ranging from 0.127 to 0.3175 mM in Gd. Solutions were placed in vials placed in a polystyrene support. MRI images of the phantoms were acquired at room temperature. MRI was performed on a 7 teslas horizontal magnet (Pharmascan, Bruker, Ettlingen). A cross coil configuration was used (volume/surface coil, Bruker, Ettlingen). For T1-weighted (T1w) images, a flow sensitive alternating inversion recovery and rapid acquisition with relaxation enhancement (FAIR-RARE) sequence was used (TR: 780 ms, TE: 4.73 ms, TI: increasing from 6.16 ms to 750 ms following a geometrical function, RARE factor of 4, image matrix: 128×128, 1 slice with a thickness of 3 mm and total acquisition time of 16 min 38 sec). Image analysis was carried out with Bruker software Paravision (version 6.0.1), MATLAB R2012b software and imageJ (version 1.50f) software. The R1 value (inverse of the calculated T1 value) was plotted as a function of the Gd concentration for each experimental point, and the slope of the line corresponded to the compound relaxivity ($s^{-1}$ $mM^{-1}$).

Fractional Cerebral Blood Volume Maps Before and after Intravenous Injection of Gas-Loaded FAU-Gd For the imaging protocol, after a scout view and a T2w-RARE8 scan, fractional cerebral blood volume (fCBV) was measured at equilibrium as previously described (Valable S et al., 2016, J Cereb Blood Flow Metab. 2017 July; 37(7):2584-2597. doi: 10.1177/0271678X16671965. Epub 2016 Jan. 1). Five T2*w (TR=20,000 ms, Number of EXcitation: NEX=3, 50 contiguous slices, resolution=0.3×0.3×0.3 mm) and four T2w (TR=20,000 ms, NEX=3) images (echo planar imaging: EPI) were acquired with various echo times (TE for T2*=12, 15, 18, 21, and 24 ms and for T2w=40, 60, 80, and 100 ms, respectively). An intravenous administration of a contrast agent (iron oxide nanoparticles P904® (200 mmol·kg−1, Guerbet Research) was then performed and a T2*w images (TE=12 ms) was acquired so as to measure cerebral blood volume (CBV) maps at rest conditions. Then, 300 µl of $CO_2$ or Carbogen loaded FAU-Gd (1%) were intravenously injected and CBV maps were measured every 5 minutes until 1 hour post-injection. Consequently, for each animal, fCBV maps were obtained under two conditions: baseline and after administration of gas loaded FAU-Gd. Image analysis was performed with in-house developed macros based on the ImageJ software (http://rsb.info.nih.gov/ij/, 1997-2014) as previously described.

Oxygen Saturation Maps Before and after Intravenous Injection of Gas-Loaded FAU-Gd Oxygen saturation ($SatO_2$MRI) maps were derived from the equation published by Christen et al (J. Cereb Blood Flow Metab. 2014 September; 34(9):1550-7. doi: 10.1038/jcbfm.2014.116. Epub 2014 Jul. 9). Briefly, $SatO_2$MRI maps were calculated as a function of the T2*w signal after correction of inhomogeneities of magnetic field (B0), blood volume fraction, and T2 effects. $SatO_2$MRI maps were generated at rest conditions and after administration of gas loaded FAU-Gd.

Statistical Analyses

Data are presented as mean±SD or SEM. Statistical analyses were obtained with JMP programs (SAS Institute).

6.2. Results

Figure 3:
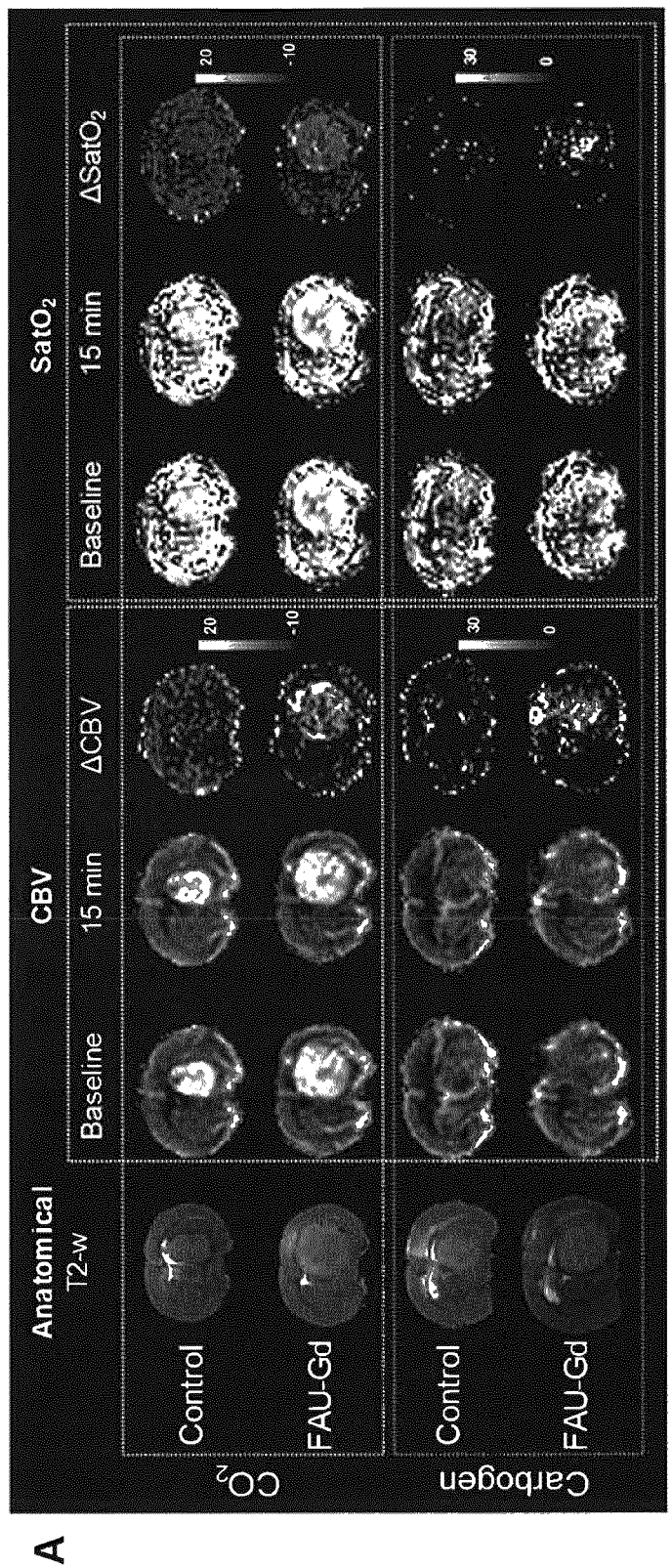
FIG. 3 (A) represents CBV and $SatO_2$MRI maps, obtained before and 15 min after intravenous injection of FAU-Gd carrying $CO_2$ or carbogen solution, T2-w anatomic image of the corresponding tumor and a map of the differences of signal between the two maps ($\Delta$CBV and $\Delta SatO_2$ respectively); (Control consisted of an injection of $H_2O$ saturated with $CO_2$ or Carbogen); (B, C) gives the quantification of the $\Delta$CBV and $\Delta SatO_2$ in the healthy relative to the tumor tissue. Mean±SEM, n=5 for control groups; n=8 for FAU-Gd—$CO_2$ group; n=5 for FAU-Gd-Carbogen group ($*p<0.02$; $**p<0.0001$, following an ANOVA); (D, E) reports the evolution over the time of the $pCO_2$ and the pH respectively in the blood of healthy Wistar rats following injection of a solution of FAU-Gd carrying $CO_2$ or $H_2O$ saturated with $CO_2$ as a control. Mean±SEM, n=5 per group ($*p<0.05$, following a two-way ANOVA); (F) represents the T2* MRI signal (reflecting the BOLD effect) measured in the venous sinus of healthy Wistar rats 4 min following an intravenous injection of $CO_2$ loaded FAU-Gd compared to FAU-Gd not loaded with $CO_2$, to water saturated with $CO_2$ and to the simple breathing of $CO_2$. Mean±SEM, n=5.
Figure 3:
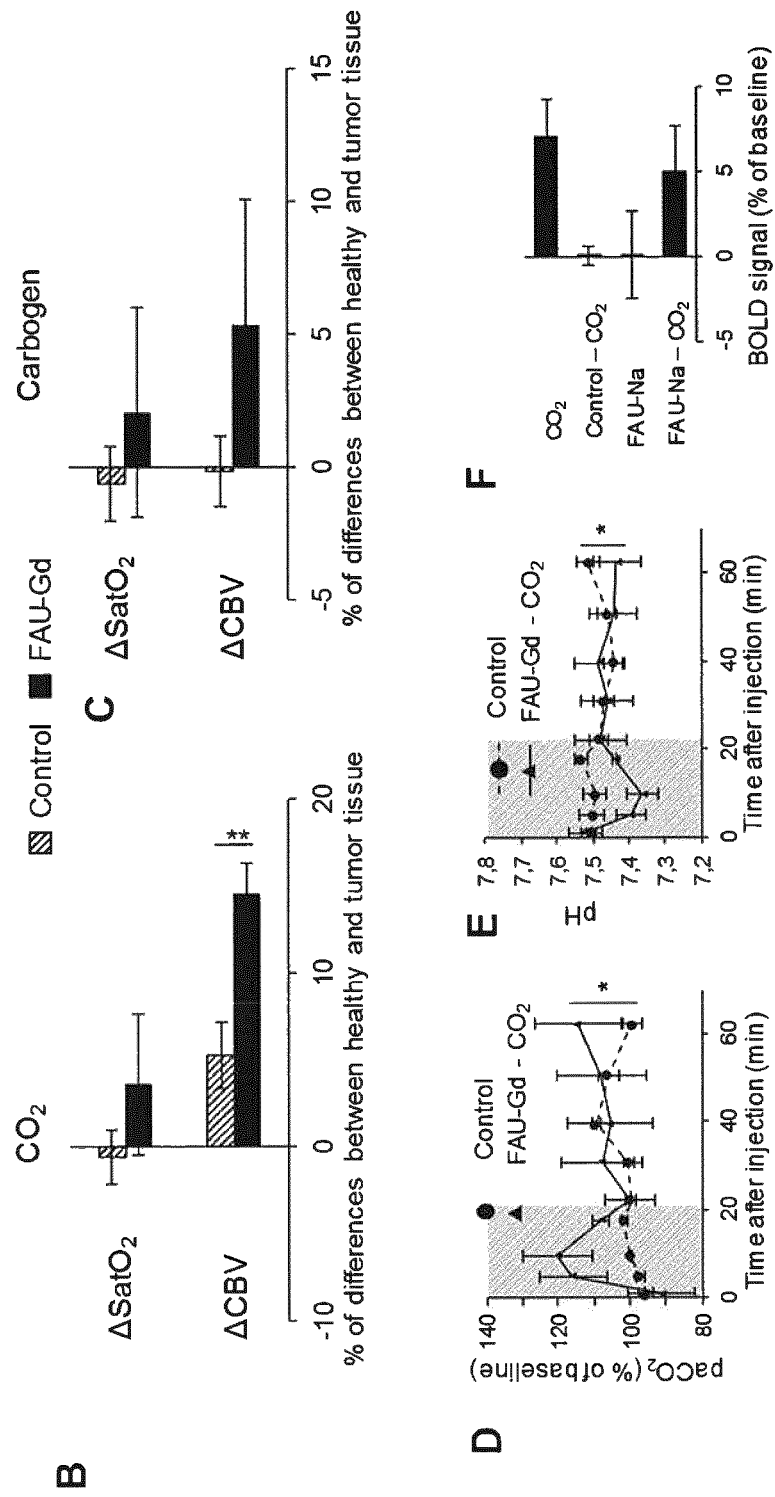

The results of measurement of the percentage of change in cerebral blood volume (CBV) following the IV injection of FAU-Gd carrying $CO_2$ or carbogen, are reported on FIG. 3 annexed. On this FIG. 3, FIG. 3(A) represents CBV and $SatO_2$MRI maps, obtained before and 15 min after intravenous injection of FAU-Gd carrying $CO_2$ or carbogen solution, T2-w anatomic image of the corresponding tumor and a map of the differences of signal between the two maps (ΔCBV and Δ$SatO_2$ respectively). Control consisted of an injection of $H_2O$ saturated with $CO_2$ or Carbogen. FIG. 3 (B, C) gives the quantification of the ΔCBV and Δ$SatO_2$ in the healthy relative to the tumor tissue. Mean±SEM, n=5 for control groups; n=8 for FAU-Gd—$CO_2$ group; n=5 for FAU-Gd-Carbogen group (*p<0.02; **p<0.0001, following an ANOVA). FIG. 3 (D, E) reports the evolution over the time of the $pCO_2$ and the pH respectively in the blood of healthy Wistar rats following injection of a solution of FAU-Gd carrying $CO_2$ or $H_2O$ saturated with $CO_2$ as a control. Mean±SEM, n=5 per group (*p<0.05, following a two-way ANOVA). FIG. 3 (F) represents the T2* MRI signal (reflecting the BOLD effect) measured in the venous sinus of healthy Wistar rats 4 min following an intravenous injection of $CO_2$ loaded FAU-Gd compared to FAU-Gd not loaded with $CO_2$, to water saturated with $CO_2$ and to the simple breathing of $CO_2$. Mean±SEM, n=5.

These results show that after 15 min, the injection of $CO_2$ loaded FAU-Gd, induces an increase in CBV inside the tumor tissue whereas it induced a decrease in the healthy tissue (FIG. 3 A, B) with a significant difference of 9.91% between the two tissues. No changes between healthy and tumor tissues were observed following injection of water saturated with $CO_2$ but also following injection of FAU-Gd unloaded with $CO_2$.

Similar results, although slightly attenuated, were observed with FAU-Gd loaded with Carbogen with a difference of 5.95% between the healthy and tumor tissue (FIG. 3 A, C).

The measurements of tissue saturation in oxygen ($SatO_2$) before and after injection of FAU-Gd carrying $CO_2$ or Carbogen were carried out to determine if the increase in CBV led to a reoxygenation of the tumor (FIGS. 3A, B and C). The results show that with FAU-Gd carrying $CO_2$, the Δ$SatO_2$ remained unchanged in the tumor whereas it induced a decrease in the healthy tissue with a significant difference of 4.53% between the two compartments. The opposite situation was observed with Carbogen, resulting in an increase in the Δ$SatO_2$ in the tumor and not in the healthy tissue resulting in a difference of 2.79% between the two compartments.

These results suggest a specific functional effect of nanosized zeolites of the invention carrying gas in the tumor. However, following intravenous injection, zeolite will experience two compartments before reaching the tumor.

The release of gas in the blood was further investigated by following the arterial partial pressure of $CO_2$ ($paCO_2$) following injection of FAU-Gd carrying $CO_2$ (FIG. 3F). An increase in the $paCO_2$ of 4 mmHg was observed reaching a peak at 10 min, paralleled by a slight acidification (FIG. 3 D, E). These changes were not observed with water saturated with $CO_2$ and FAU-Gd unloaded with $CO_2$.

While the breathing of 5% of $CO_2$ (used as a control) induced an increased in the BOLD signal of 7.06±2.25%, the intravenous injection of nanosized zeolites $CO_2$-loaded FAU-Gd resulted in an increase in the BOLD signal of 5.05±2.65%. Injection of water saturated with $CO_2$ or nanosized zeolites without $CO_2$ failed to modify the BOLD signal These data allow to postulate that a release of gas occurs into the systemic circulation but the specific accumulation of nanosized zeolites into the tumor tissue may be sufficient to successfully deliver gas within the tumor which in turn increases blood volume and oxygenation. These data also suggest that nanosized zeolites accumulate specifically within the tumoral tissue and not in the healthy brain.

Figure 4:
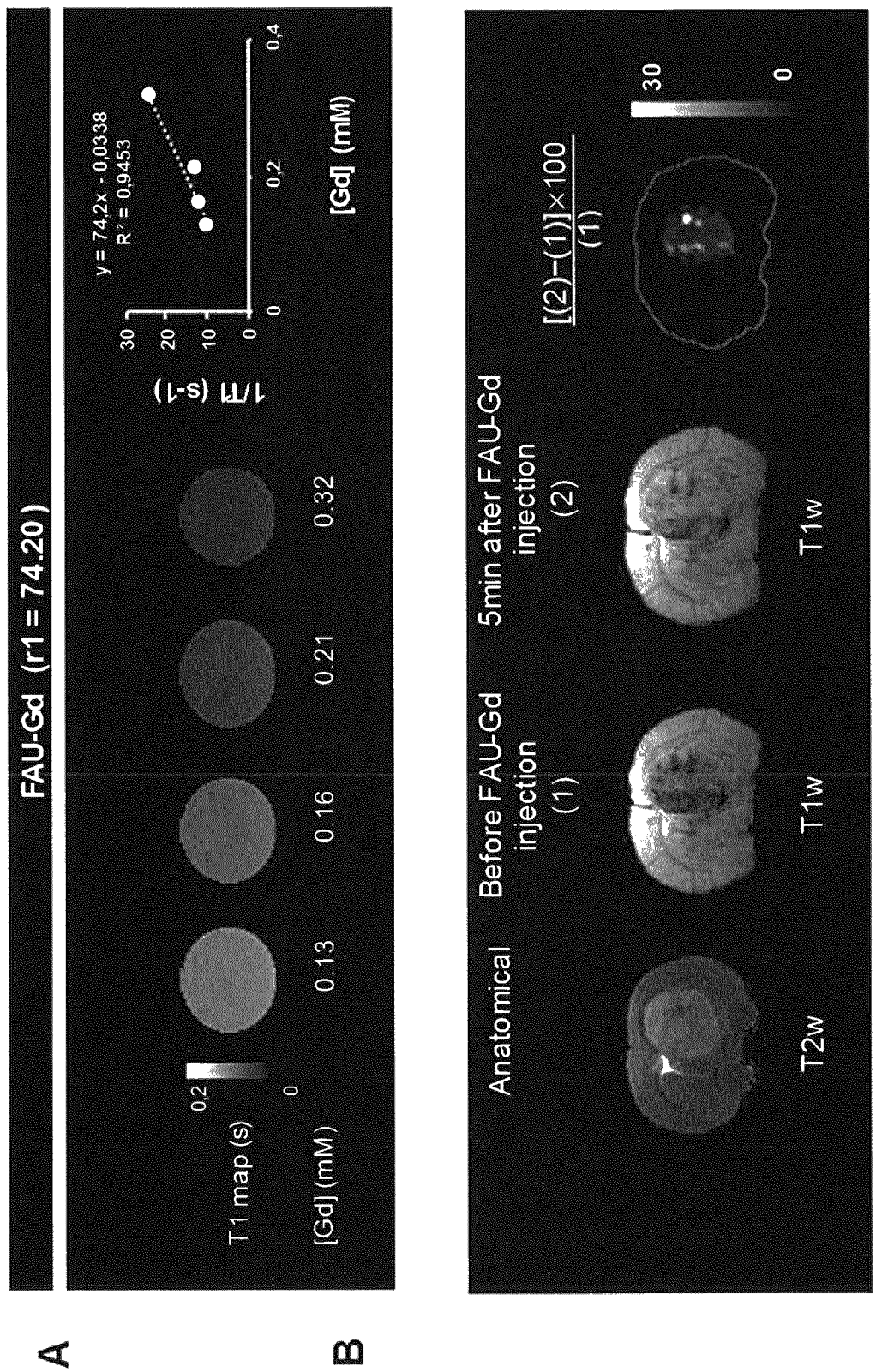
FIG. 4 represents (A) relaxivity in vitro measurements at room temperature at 7 teslas. The calculated r1 parameter of the FAU-Gd nanosized zeolites was 74.2 mM−1.s−1; (B) from left to right respectively T2w anatomic image of the tumor, T1-w images acquired before (top left) or 5 min after (top right) intravenous injection of 300 µl of a FAU-Gd solution (1%); (lower left) and a map of the differences of signal between the two T1-w images; (C) the results of the quantification over the time of the T1-w signal intensity in the healthy and the tumor tissue following an intravenous injection of 300 µl of a FAU-Gd solution (1%). The arrow indicates the time of injection. Mean±SEM; n=5. Two-way ANOVA ($*p<0.0001$, tissue effect and time effect).
Figure 4:
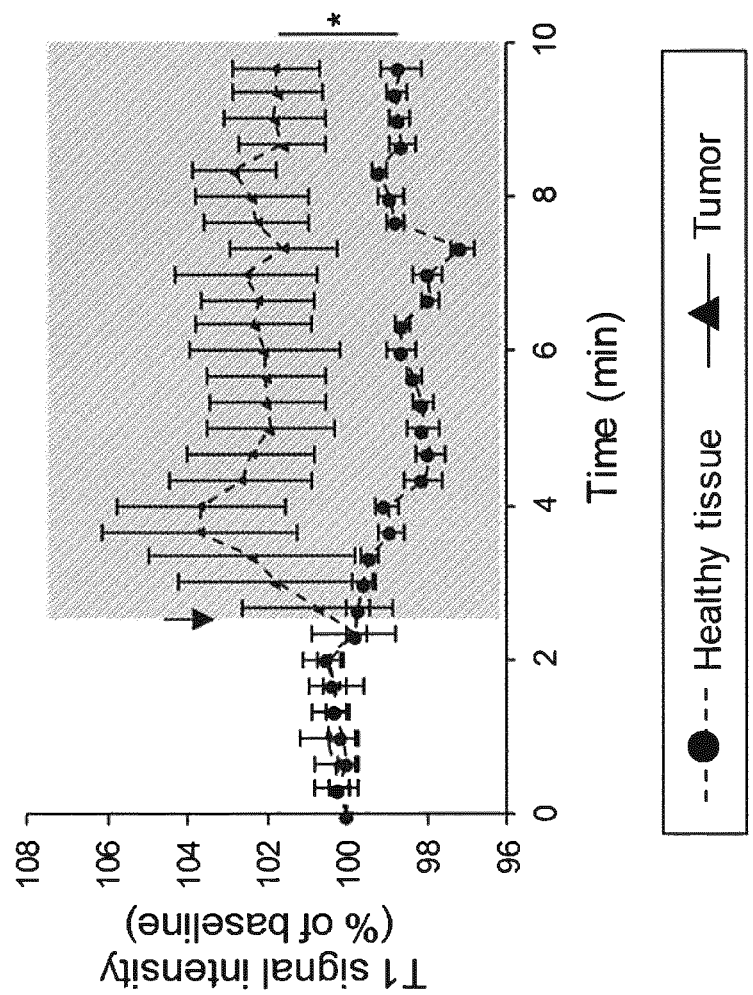

The results of the distribution of FAU-Gd in the brain following an intravenous injection are given on FIG. 4.

FIG. 4A represents relaxivity in vitro measurements at room temperature at 7 teslas. The calculated r1 parameter of the FAU-Gd nanosized zeolites was 74.2 mM−1·s−1.

FIG. 4B represents from left to right respectively T2w anatomic image of the tumor, T1-w images acquired before (top left) or 5 min after (top right) intravenous injection of 300 µl of a FAU-Gd solution (1%); (lower left) and a map of the differences of signal between the two T1-w images. FIG. 4C gives the results of the quantification over the time of the T1-w signal intensity in the healthy and the tumor tissue following an intravenous injection of 300 µl of a FAU-Gd solution (1%). The arrow indicates the time of injection. Mean±SEM; n=5. Two-way ANOVA (*p<0.0001, tissue effect and time effect).

These results show that nanosized zeolites according to the present invention are likely to extravasate and accumulate in the tumor tissue but not to cross the blood brain barrier. This hypothesis has been verified, thanks to the presence of gadolinium in the zeolite, by dynamic T1-weighted MRI to detect FAU-Gd after an IV injection (FIG. 4 B,C). The results clearly show that a hyper-signal appears following the injection that is circumscribed inside the tumor. The difference between the T1-w images acquired after and before the injection (FIG. 4B, right image) demonstrates that FAU-Gd efficiently reached the tumor and not the surrounding healthy tissue. The quantification of the signal over the time show that the increase is slightly delayed and occurs about 30 s following the injection of FAU-Gd with a maximum increase of 3.67±1.36% of the baseline obtained after about 1 min40 s (FIG. 4C). These data strongly suggest the capacity of the nanosized FAU-Gd to specifically target brain tumors.

It is interesting to note that despite gadolinium accounts for only 3.33% of the zeolite weight, it is possible to detect it with MRI. The quantity of gadolinium that has to be injected to obtain signal is therefore low for FAU-Gd, probably due to a good access of water molecules to gadolinium atoms. This is of great importance in a context of concerns that are now being raised about the stability of gadolinium chelates complex currently in use and a link with suspected adverse effects as well as accumulation of gadolinium in various tissues including the brain.

Overall, these data show the ability of the nanosized FAU-Gd according to the invention to carry $CO_2$ or Carbogen resulting in functional effects on blood volume and oxygenation between the healthy and the tumor tissue.

Figure 5:
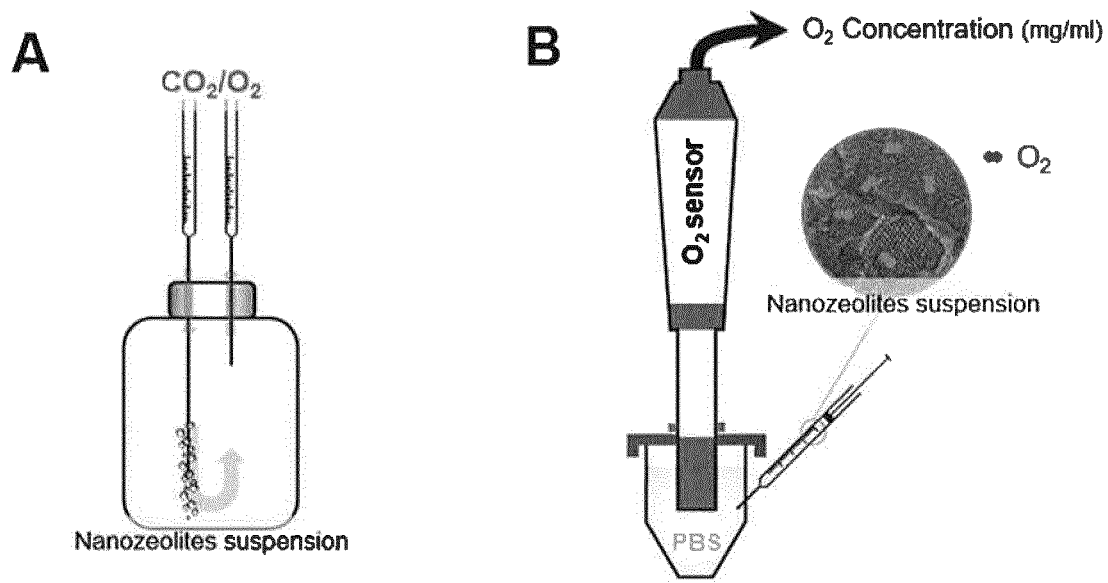
FIG. 5 represents (A) Experimental set-up used to load nanozeolites with gases (CO2 and/or O2). The flowrate was 1 l/min and the duration was fixed at 30 minutes; (B) Experimental set-up used to assess the ability of nanozeolites to release their oxygen payload. 12 ml of buffer (phosphate buffered saline) solution is kept in a closed tube linked to an oxygen sensor. Then, zeolites loaded with oxygen are injected into the buffer solution through a needle and the reoxygenation of the buffer is continuously monitored. Of note, this experimental set-up can be used in an hypoxic chamber so as to strictly control the oxygenation of the buffer before injection of nanozeolites; (C) Representation of the reoxygenation ability of nanozeolites as a function of the initial buffer oxygenation (21%; 5%; 1% and 0.1%) and as a function of time. Oxygen concentration was measured 30 minutes before nanozeolites injection in the system and 60 minutes after; (D) The more the initial oxygenation is low, the more nanozeolite release oxygen. The similar experimental set-up was used as described in (B); (D) Quantification of oxygen released from zeolites in a buffer solution (phosphate buffered saline, pH=7.2, 37° C., initial oxygen concentration 0.1%) as a function of the charge balancing cation and as a function of time. The similar experimental set-up was used as described in (B).
Figure 5:
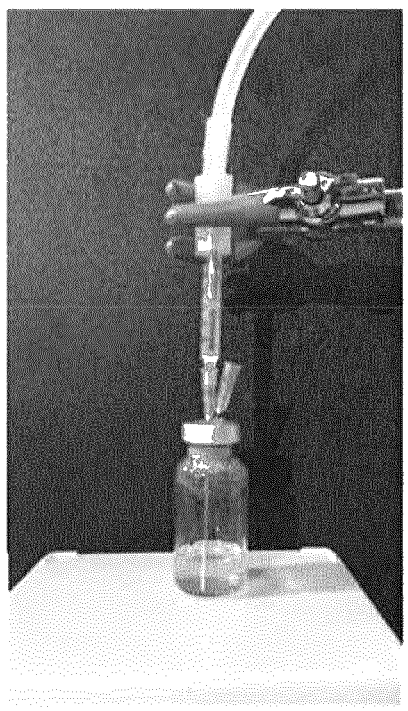
Figure 5:
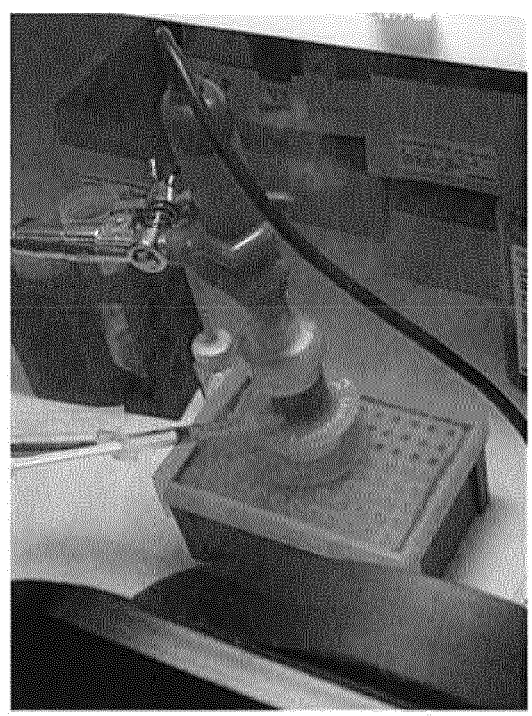
Figure 5:
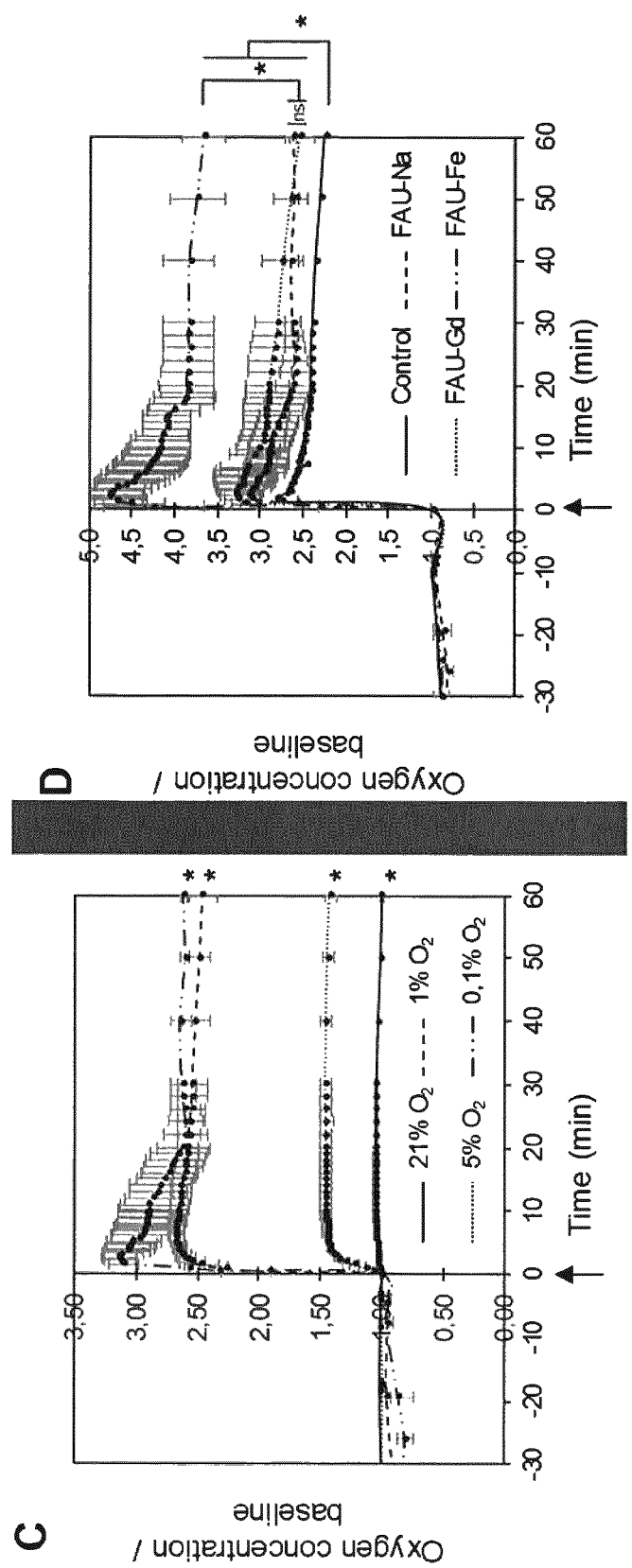

Example 7: Study of the Release of Oxygen by Zeolites in Aqueous and Hypoxic Conditions 7.1. Materials and Methods A hypoxia chamber (IN VIVO2 500™, 3M) was used to get a stable and precisely controlled gas composition of the atmosphere with a precision of 0.1% $O_2$ by adapting the amount of $N_2$. PBS (Phosphate buffered saline, Sigma-Aldrich) solution was equilibrated with the gas mixture contained in the hypoxia chamber for 1 h prior to the experiment. A closed reaction vessel containing 12 ml of equilibrated PBS at 37° C., and a dissolved oxygen sensor (SevenGo (Duo) Pro™/OptiOx™, Mettler Toledo) was used inside the hypoxia chamber. Prior to the experiment, baseline was established by measuring the oxygen saturation in the system for 30 min. Oxygen-loaded nanozeolites (FIG. 5A) were then added to the system and dissolved oxygen in the PBS solution was measured continuously for 1 h (FIG. 5B). The oxygen release capacity of FAU nanosized zeolites with different cations composition (FAU-Na as prepared in example 1 used as a reference not forming part of the present invention, FAU-Fe and FAU-Gd as prepared according to example 1 but forming part of the present invention) was compared to pure water saturated with oxygen as a control. The oxygen release capacity of FAU-Na nanozeolites was compared for decreasing levels of oxygen in the atmosphere (21, 5, 1 and 0.1% of 02).

7.2. Results

Experiments were performed at various percentage of oxygen by replacing oxygen by nitrogen in the incubator so as to mimic hypoxic conditions that could be observed in tumor situations.

When experiments were performed at 21% (normoxic condition), almost no release of oxygen occurred in the medium when $O_2$ loaded FAU-Na were delivered (FIG. 5C). When 5% or 1% of oxygen was used, the oxygen release became more prominent and reached a maximum when oxygen concentration was 0.1%.

The release of oxygen depending on the nature of the carrier was analyzed too. The results show that the control, consisting of water saturated with oxygen, is by itself able to provide oxygen in the system. The amount of oxygen increases by 2.82±0.13 times from the baseline after saturated water injection.

However, when $O_2$ loaded FAU-Na nanocrystals were injected, the amount of oxygen in the system is significantly higher compared to the control as the concentration increases up to 3.13±0.14 times from the baseline.

The zeolite nanocrystals containing gadolinium and iron were also evaluated. The results show that the addition of gadolinium does not significantly change the amount of $O_2$ released compared to FAU-Na zeolites. On the other hand, the addition of iron in zeolites strongly increases their ability to release oxygen. The oxygen concentration increases to a maximum of 4.76±0, 38 times for FAU-Fe compared to the baseline.

Regarding the kinetics of gas release, the profile is substantially the same for the four conditions. Gas release occurs very quickly, the maximum is reached about 2 min after the injection into the system.

Example 8: Comparison of $O_2$ Release Capacity of FAU-Na, FAU-Gd and FAU-Fe Zeolite Samples In the following, FAU-Na is prepared as in example 1 and used as a reference, not forming part of the present invention.

FAU-Fe and FAU-Gd are prepared according to example 1 and are part of the present invention.

In-situ adsorption of $CO_2$ and $O_2$ on nanosizedzeolites: Powder samples of as prepared and ion-exchanged zeolites were pressed (~$10^7$ Pa) into self-supported disks (2 $cm^2$ area, 20 mg·$cm^{-2}$). Fourier-transform infrared (FTIR) spectra were recorded using a Nicolet 6700 IR spectrometer equipped with a mercury cadmium telluride (MCT) detector and an extended KBr beam splitter. Spectra were recorded in the 400-5500 $cm^{-1}$ range at 4 $cm^{-1}$ with 128 scans. The in situ was evacuated or flooded with different gases and also heated up to 577° C. was used. The samples were activated at 225° C. for 2 h under vacuum. Various amounts of $CO_2$ (at 25° C.) or $O_2$ (at −196° C.) were introduced into the cell and kept in equilibrium for 5 minutes at the corresponding temperatures before recording each spectrum. All the spectra were normalized to the sample's mass and plotted as absorbance per gram over the wavelength.

Figure 6:
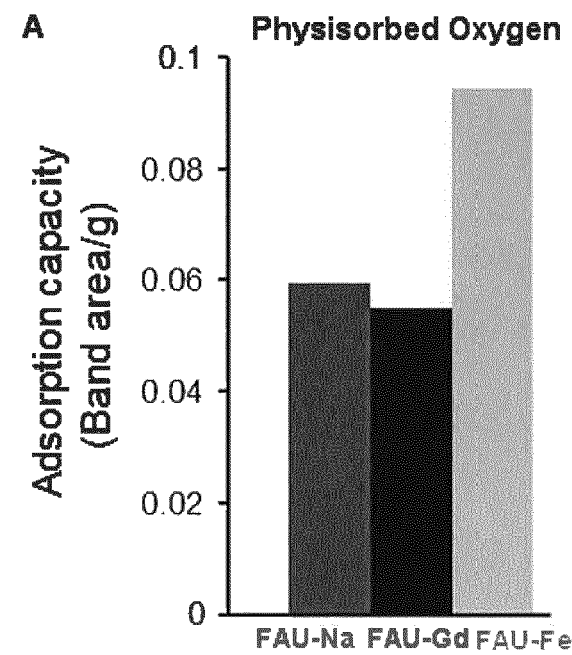
FIG. 6 represents (A) physisorbed $O_2$ measured at −196° C. on nanosized FAU-Na—X, FAU-Gd, and FAU-Fe zeolites; (B) the quantification of oxygen released from zeolites in a buffer solution (phosphate buffered saline, pH=7.2, 37° C. as a function of the charge balancing cation(*p<0.05; ANOVA). Mean±s.d., n=3/condition. The result show the absolute quantification of oxygen release and the value of saturated water alone was deducted.
Figure 6:
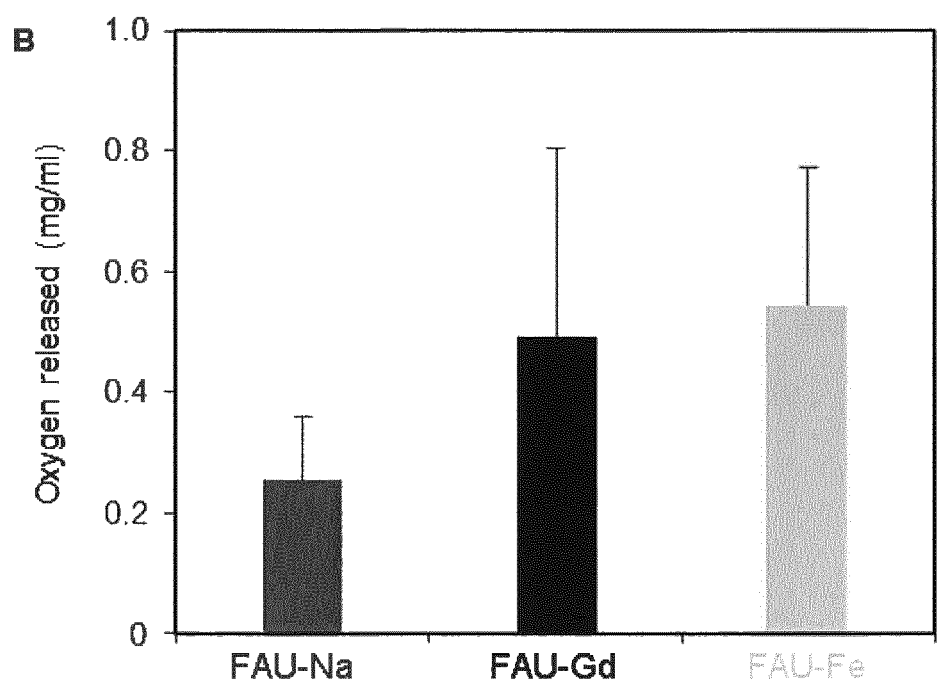

The physisorbed $O_2$ and physi- or chemisorbed $CO_2$ were also evaluated by in-situ IR spectroscopy following the introduction of controlled quantities of the desired gas into the zeolite samples. The $CO_2$ loading capacity of zeolites samples follows the trend FAU-Fe>FAU-Na>FAU-Gd. Despite the lower quadrupole moment of oxygen compared to $CO_2$ which renders it less efficient for adsorption on zeolites, small amount of iron (1.7 wt. %, measured with ICP-AES, see table 1) introduced in the zeolite (Fe—X) substantially improved the $O_2$ adsorption capacity in comparison to the FAU-Na and FAU-Gd zeolite samples (FIGS. 6A and 6B).

The $O_2$ release capacity of FAU-Na, FAU-Gd and FAU-Fe zeolite samples was then compared at 0.1% of $O_2$. To differentiate the quantity of oxygen provided by the zeolites from the oxygen provided by the dispersing solution (pure water), the values were deducted from the value of saturated water alone. Samples FAU-Na, FAU-Gd and FAU-Fe deliver to the system 0.26, 0.49 and 0.54 mg of oxygen per ml, respectively, as shown in FIG. 6B. These results clearly show that the FAU-Gd and FAU-Fe zeolites deliver more oxygen than the FAU-Na zeolite. Thus, FAU-Na, FAU-Gd and FAU-Fe zeolites transport 19, 37 and 41 mmol of $O_2$/g respectively, which is higher than the values recorded for HEMOXYCarrier®, a natural giant extracellular haemoglobin from polychaete annelids and Polymer Hollow Microparticles (PHM).

The invention claimed is:

1. A method for the preparation of a colloidal aqueous suspension of stable zeolite single nanocrystals with monodisperse particle size distribution ranging from 5 to 200 nm, said stable zeolite single nanocrystals having a three-dimensional framework comprising silicon or silicon and aluminum, said framework comprising channels and cavities at least partially filled with at least one gas of $O_2$ or $CO_2$ and at least one cation C of Gd, Fe, Cu, or Ce in an amount ranging from about 0.1 to about 10 weight % with respect to the total mass of said nanocrystals, wherein said method comprises the following steps:
   1) subjecting a colloidal suspension CS1 of at least one type of stable zeolite single nanocrystals with monodisperse particle size distribution ranging from about 5 to 200 nm, said stable zeolite single nanocrystals having a three-dimensional framework comprising at least one of silicon or aluminum, said framework comprising channels and cavities and alkali metal cations M, to an ion exchange of at least a part of the alkali metal cations M with at least one cation C of Fe, Gd, Cu, or Ce, to obtain a colloidal suspension in water CS2 of zeolite single nanocrystals having a three-dimensional framework comprising channels and cavities, and at least one cation C of Fe, Gd, Cu, or Ce in an amount ranging from 0.1 to 10 weight % with respect to the total mass of the zeolite single nanocrystals;
   wherein step 1) is carried out by adding to the colloidal suspension CS1, a solution containing at least one salt of a cation C of Fe, Gd, Cu, or Ce;
   2) purifying the colloidal suspension CS2 of zeolite single nanocrystals obtained in step 1) with water until a pH ranging from 6.5 to 7.5 is reached; and
   3) contacting the purified colloidal suspension of zeolite single nanocrystals obtained in step 2) with at least one gas of $O_2$ or $CO_2$.

2. The method according to claim 1, wherein the amount of cation C ranges from 1 to 5 weight % with respect to the total amount of the zeolite single nanocrystals.

3. The method according to claim 1, wherein the concentration of the salt of cation C in the solution that is added into the suspension CS1 ranges from 1 to 10 mM.

4. The method according to claim 1, wherein the salt of the cation C comprises $C(NO_3)_3 \cdot nH_2O$, wherein C=Gd, Fe, Ce or Cu.

5. The method according to claim 1, wherein the zeolite single nanocrystals present in the colloidal suspension CS1 comprise:
   zeolite single nanocrystals having a FAU- or an EMT-three-dimensional framework of $SiO_2$ and $Al_2O_3$ tetrahedra;
   zeolite single nanocrystals having an MFI-three-dimensional framework of $SiO_2$ tetrahedra; or
   zeolite single nanocrystals having an LTL-three-dimensional framework of $SiO_2$ and $Al_2O_3$ tetrahedra.

6. The method according to claim 5, wherein the zeolite single nanocrystals present in the colloidal suspension CS1 used in step 1) has a FAU-type or an EMT-type three-dimensional framework.

7. The method according to claim 1, wherein step 2) is a washing step by double distilled water and is repeated until the pH of the colloidal suspension CS2 reaches a value of 7±0.2.

8. The method according to claim 1, wherein step 3) is performed by bubbling the colloidal suspension CS2 with pure $O_2$, pure $CO_2$, or with a mixture composed of about 95% by volume of $O_2$ and of about 5% by volume of $CO_2$.

9. A colloidal aqueous suspension of a zeolite material prepared according to the method as defined in claim 1, wherein:
   said zeolite material is the form of stable zeolite single nanocrystals with monodisperse particle size distribution ranging from 5 to 200 nm,
   said stable zeolite single nanocrystals has a three-dimensional framework comprising silicon or silicon and aluminum, said framework comprising channels and cavities at least partially filled with at least one gas of $O_2$ and $CO_2$, and
   said framework comprises at least one cation C of Fe, Gd, Cu, or Ce in an amount ranging from 0.1 to 10 weight % with respect to the total mass of said nanocrystals.

10. The colloidal aqueous suspension according to claim 9, wherein the amount of cation C ranges from 1 to 5 weight % with respect to the total mass of said nanocrystals.

11. The colloidal aqueous suspension according to claim 9, wherein the cation C comprises at least one of Gd or Fe.

12. The colloidal aqueous suspension according to claim 9, wherein said cation C is Gd and the amount of Gd ranges from 1.2 to 1.9% by mass with respect to the total mass of the zeolite material.

13. The colloidal aqueous suspension according to claim 9, wherein said cation C is Fe, and the amount of Fe ranges from 0.9 to 2% by mass with respect to the total mass of the zeolite material.

14. The colloidal aqueous suspension according to claim 9, wherein said zeolite material comprises a mixture of cations Gd and Fe, the amount of Gd ranges from 1 to 5% by mass with respect to the total mass of the synthetic zeolite material and the amount of Fe ranges from 0.9 to 2% by mass with respect to the total mass of the zeolite material.

15. A composition for at least one of therapy or diagnosis comprising a colloidal aqueous suspension of a zeolite material in the form of stable zeolite single nanocrystals as defined in claim 9.

16. A composition for cancer therapy or treatment of hypoxia-related diseases composition comprising the composition according to claim 15.

17. A composition for diagnosis of brain tumors comprising the composition according to claim 15.

18. A contrast agent in imaging comprising the colloidal aqueous suspension of a zeolite material in the form of stable zeolite single nanocrystals as defined in claim 9, wherein the cation C comprises at least one of Gd or Fe.

19. A pharmaceutical composition comprising:
   a colloidal aqueous suspension of a zeolite material in the form of stable zeolite single nanocrystals as defined in claim 9, and
   a pharmaceutical carrier.

20. The pharmaceutical composition according to claim 19, wherein said composition is an injectable composition.

21. A diagnosis composition comprising:
   a colloidal aqueous suspension of a zeolite material in the form of stable zeolite single nanocrystals as defined in claim 9, wherein cation C comprises at least one of Gd or Fe, and
   a biocompatible carrier.

22. The diagnosis composition according to claim 21, wherein said composition is an MRI diagnosis composition.

* * * * *